(12) United States Patent
Walter et al.

(10) Patent No.: US 6,923,926 B2
(45) Date of Patent: Aug. 2, 2005

(54) METHOD AND APPARATUS FOR FORMING TOW-BASED ABSORBENT STRUCTURES WITH A SINGLE CASING SHEET

(75) Inventors: John Walter, Renfrew, PA (US); John Litvay, Downingtown, PA (US); Walter Egyed, Burgettstown, PA (US)

(73) Assignee: Paragon Trade Brands, Inc., Norcross, GA (US)

( * ) Notice: Subject to any disclaimer, the term of this patent is extended or adjusted under 35 U.S.C. 154(b) by 78 days.

(21) Appl. No.: 10/394,588

(22) Filed: Mar. 24, 2003

(65) Prior Publication Data

US 2003/0212376 A1 Nov. 13, 2003

Related U.S. Application Data

(63) Continuation-in-part of application No. 10/046,279, filed on Jan. 16, 2002, now Pat. No. 6,832,905.

(51) Int. Cl.[7] .............................................. B27N 3/00
(52) U.S. Cl. ................... 264/119; 264/517; 425/80.1; 425/403.1; 425/405.1; 425/470; 156/200; 156/204; 156/227; 156/442.1; 156/442.2; 156/443; 156/578
(58) Field of Search ......................... 425/80.1, 403, 425/403.1, 405.1, 470; 264/112, 119, 517; 156/245, 442.1, 442.2, 443, 446, 578, 200, 204, 227, 438

(56) References Cited

U.S. PATENT DOCUMENTS

| | | |
|---|---|---|
| 3,973,703 A | 8/1976 | Peschl |
| 4,289,130 A | 9/1981 | Usami et al. |
| 4,468,845 A | 9/1984 | Harris |
| 4,646,342 A | 2/1987 | Hargrave et al. |
| 4,800,102 A | 1/1989 | Takada |
| 4,990,541 A | 2/1991 | Nielsen et al. |
| 5,098,423 A | 3/1992 | Pieniak et al. |
| 5,281,207 A | 1/1994 | Chmielewski et al. |
| 5,331,976 A | 7/1994 | St. Pierre |
| 5,350,370 A | 9/1994 | Jackson et al. |
| 5,436,066 A | 7/1995 | Chen |
| 5,451,882 A | 9/1995 | Wakino et al. |
| H1565 H | 7/1996 | Brodof et al. |
| 5,532,604 A | 7/1996 | Nagata |
| 5,558,713 A | 9/1996 | Siegfried et al. |
| 5,562,646 A | 10/1996 | Goldman et al. |
| 5,614,147 A | 3/1997 | Pelley |
| 5,762,844 A * | 6/1998 | Van Himbergen et al. .. 264/112 |
| 5,863,288 A | 1/1999 | Baker |
| 6,068,620 A | 5/2000 | Chmielewski |
| 6,139,912 A | 10/2000 | Onuschak et al. |
| 6,253,431 B1 | 7/2001 | Ames et al. |
| 6,497,032 B2 * | 12/2002 | Maxton et al. ............... 29/429 |
| 6,641,695 B2 * | 11/2003 | Baker ......................... 156/265 |
| 6,699,166 B2 * | 3/2004 | Walter et al. ............... 493/446 |
| 2003/0042660 A1 * | 3/2003 | Venturino et al. .......... 264/517 |

* cited by examiner

*Primary Examiner*—Donald Heckenberg
(74) *Attorney, Agent, or Firm*—Hunton & Williams

(57) ABSTRACT

An apparatus and method for forming tow-based absorbent structures having a single casing sheet are disclosed. The apparatus has a tow supply mechanism for providing tow material, a particulate matter supply mechanism for providing particulate matter, and a casing sheet supply mechanism for providing casing sheet material. The apparatus also has a vacuum draw roll having a foraminous center surface that has a width defined by a first edge and a second edge and is rotatable about a first axis. The vacuum draw roll is positioned to receive the tow material, the particulate matter and the casing sheet material to form a open core composite supply. The apparatus also has one or more angled surfaces positioned to create one or more obtuse angles in the open core composite supply, and one or more folders to further fold the one or more obtuse angles in the open core composite supply to form a folded core composite supply.

33 Claims, 16 Drawing Sheets

METHOD AND APPARATUS FOR FORMING TOW-BASED ABSORBENT STRUCTURES WITH A SINGLE CASING SHEET

This application is a continuation-in-part of U.S. Ser. No. 10/046,279, filed Jan. 16, 2002, now U.S. Pat. No. 6,832,905.

FIELD OF THE INVENTION

The present invention relates generally to systems and methods for manufacturing absorbent garment cores. More specifically, the present invention relates to a system and method for forming tow-based absorbent structures having a single casing sheet.

BACKGROUND OF THE INVENTION

Disposable absorbent garments such as infant diapers or training pants, adult incontinence products and other such products typically were constructed with a moisture-impervious outer backsheet, a moisture-pervious body-contacting inner topsheet, and a moisture-absorbent core sandwiched between the liner and backsheet.

Much effort has been expended to find cost-effective materials for absorbent cores that display good liquid absorbency and retention. Particles of superabsorbent materials (SAP) in the form of granules, beads, fibers, bits of film, globules, etc., have been favored for such purposes. Such SAP materials generally are polymeric gelling materials that are capable of absorbing and retaining even under moderate pressure large quantities of liquid, such as water and body wastes, relative to their weight. The SAP particles typically have been distributed within a fibrous web of fluffed pulp material, which may comprise natural or synthetic fibers. Such absorbent structures are commonly referred to as fluff pulp/SAP cores.

Superabsorbent material generally is a water-insoluble but water-swellable polymeric substance capable of absorbing water in an amount that is greater than the weight of the substance in its dry form. In one type of superabsorbent material, the particles may be described chemically as having a back bone of natural or synthetic polymers with hydrophilic groups or polymers containing hydrophilic groups being chemically bonded to the back bone or an intimate admixture therewith. Included in this class of materials are modified polymers such as sodium neutralized cross-linked polyacrylates and polysaccharides including, for example, cellulose and starch and regenerated cellulose that are modified to be carboxylated, phosphonoalkylated, sulphoxylated or phosphorylated, causing the SAP to be highly hydrophilic. Such modified polymers also may be cross-linked to reduce their water-solubility.

The ability of a superabsorbent material to absorb liquid is dependent upon the form, position and/or manner in which particles of the superabsorbent material are incorporated into the fibrous web of the absorbent core. Whenever a particle of the superabsorbent material is wetted, it swells and forms a gel. Gel formation can block liquid transmission into the interior of the absorbent core, a phenomenon called "gel blocking." Gel blocking prevents liquid from rapidly diffusing or wicking past the "blocking" particles of superabsorbent, causing portions of a partially hydrated core to become inaccessible to multiple doses of urine. Further absorption of liquid by the absorbent core must then take place via a diffusion process. This is typically much slower than the rate at which liquid is applied to the core. Gel blocking often leads to leakage from the absorbent article well before all of the absorbent material in the core is fully saturated.

Despite the incidence of gel blocking, superabsorbent materials are commonly incorporated into absorbent cores because they absorb and retain large quantities of liquid, even under load. However, in order for superabsorbent materials to function, the liquid being absorbed in the absorbent structure must be transported to unsaturated superabsorbent material. In other words, the superabsorbent material must be placed in a position to be contacted by liquid. Furthermore, as the superabsorbent material absorbs the liquid it must be allowed to swell. If the superabsorbent material is prevented from swelling, such as by being tightly constrained within the fibrous web or by pressure exerted by the swelling of adjacent superabsorbent particles, it will cease absorbing liquids.

Adequate absorbency of liquid by the absorbent core at the point of initial liquid contact and rapid distribution of liquid away from this point are necessary to ensure that the absorbent core has sufficient capacity to absorb subsequently deposited liquids. Previous absorbent cores have thus attempted to absorb quickly and distribute large quantities of liquids throughout the absorbent core while minimizing gel blocking during absorption of multiple doses of liquid.

Some of the more important performance attributes of an absorbent core of a diaper (or any other absorbent garment) are functional capacity, rate of absorption, and core stability in use. Absorption under load or AUL is a good measure of functional capacity and the rate at which that absorption occurs. AUL is a function of both SAP basis weight (mass per unit area) and the composition of SAP used in the composite. Conventional baby diaper cores that contain only a fibrous web of fluff pulp and a high gel strength SAP typically maintain adequate SAP efficiency if the core contains less than about 50% SAP. Fluff/SAP diaper cores containing more than 50% SAP generally result in lower SAP efficiency because of gel blocking. Although fluff/SAP cores at greater than 50% SAP can provide adequate absorbency, the overall basis weight of the core typically must be increased to compensate for the lower efficiency of the SAP. Increasing the basis weight decreases the performance/cost ratio of the absorbent core, making them uneconomical. Also, increased basis weights tend to affect the fit and comfort of the garment, as well as impacting the packaging and shipping costs.

Attempts to increase the relative weight of SAP by reducing the basis weight of the conventional fluff pulp have resulted in failure because low density fluff pulp mats have been unable to withstand the tensile loads placed on them during the manufacturing process. Such cores also exhibit poor wet strength, making them unstable during use, and fail to adequately secure the SAP in place. The introduction of relatively high integrity fibrous structure cores, however, has allowed the basis weight of the fibrous web to be decreased without compromising the manufacturability and wet strength of the absorbent core. These absorbent core structures have improved SAP efficiency and a lower overall basis weight. Such absorbent cores are disclosed, for example, in U.S. Statutory Invention Registration No. H1,565 to Brodof et al., which is incorporated by reference herein in its entirety and in a manner consistent with the present invention. These high integrity fibrous structure cores, referred to herein as "tow/SAP" cores or "tow-based" cores, typically use a continuous tow of crimped filaments. The tow may be provided to the absorbent core manufacturer in a compact form and "opened" (i.e., "bloomed" or fluffed up) prior to being assembled into an absorbent core.

In some cases, the fibrous web of the tow/SAP core may be treated with a tackifying agent to adhere the SAP particles to the fibrous web. In other cases, the SAP particles may be introduced into the fibrous web without any adhesive, binder or tackifying agent, such as is disclosed in U.S. Pat. No. 6,068,620 issued to Chmielewski et al., which is incorporated by reference herein in its entirety and in a manner consistent with the present invention. Such a construction has been referred to as a dry-formed composite (DFC) core. A DFC core may be surrounded by a tissue layer or multiple tissue layers to form a DFC laminate structure that contains the fibrous web and SAP. One potential drawback with DFC cores, however, is that known methods and apparatus for producing such cores typically require two separate tissue sheets to be used during manufacturing to encase the tow and SAP. The use of two tissue sheets may, for example, increase the cost or complexity of the manufacturing operation.

A problem with SAP-containing fibrous cores has been to provide the SAP into the fibrous web in a controlled manner. Typical known processes for creating a conventional fluff pulp/SAP core use a large forming chamber to blend the SAP with the fluffed pulp, then convey this blend onto a drum or screen by using a vacuum. The drum or screen has forming pockets that form the fluff pulp/SAP material into the desired shape and the formed cores then are deposited for integration into absorbent products. Such methods have been found to be inefficient during startup and transitions in the manufacturing line speed because they require a relatively large amount of time to provide a stabilized mixture of SAP and fluff pulp, leading to the creation of a large number of scrap products until stabilization.

Other conventional processes for forming fluff pulp/SAP cores immerse the fluffed pulp in a fluid mixture containing SAP particles, then dry the fluff pulp/SAP mixture before integration into the absorbent article. Such wet forming processes typically require more manufacturing steps and are more expensive than dry forming methods.

Other feeding systems use fixed-size moving mechanical gates that provide a uniform amount of SAP to the absorbent core, such as is disclosed in U.S. Pat. No. 6,139,912 to Onuschak et al., which is incorporated herein by reference in its entirety and in a manner consistent with the present invention. Although such devices may be suitable for providing an even flow of SAP or other powdered and particulate additives to absorbent cores, they rely on relatively complex feeding machinery, including a rotary valve that uses a pneumatic SAP conveyor to return undistributed SAP back to a supply container. Pneumatic conveyors typically require a relatively long time to become pressurized and to convey the SAP, causing inefficiencies during transitional phases, such as when the machine operating speed varies, such as during start-up and shut-down, or when it is desired to change the amount of SAP being fed to the core. The additional parts of such feeders may also be expensive and subject to wear and other service problems. Similar devices, having similar deficiencies, are disclosed in U.S. Pat. No. 4,800,102 to Takada, which is incorporated herein by reference in its entirety and in a manner consistent with the present invention.

Still other feeding systems use pneumatic particle projectors that use pressurized gas to convey the SAP to the surface of the absorbent core. Such devices are disclosed, for example, in U.S. Pat. Nos. 5,614,147 to Pelley and 5,558,713 to Siegfried et al., which are incorporated herein by reference in their entirety and in a manner consistent with the present invention. Such systems rely on relatively complex air conveyors, that may be susceptible to blockage and may not efficiently accommodate as wide a variety of particulate, powder and fibrous materials as other systems due to their relatively small passage sizes. Indeed, it has been found that the compressed air used in such pneumatic conveyors is often contaminated with oil that may cause blockage, SAP degradation, and other problems. Such systems may also require a relatively long time to stabilize, leading to inefficiencies during transitional phases.

Other known SAP feeding systems are disadvantageous for a number of reasons. First, the mixture of fiber and SAP still is subject to local concentrations and shortages of SAP. Second, these feeding systems typically can not be controlled accurately enough to provide concentrations and shortages of SAP when they are desired. Third, such feeding systems can not be controlled to accurately provide reduced SAP amounts that are necessary during transitional phases, leading to improperly loaded cores during those phases of operation.

These are just a few of the disadvantages of the prior art which the preferred embodiments seek to address. The foregoing description of certain material, methods and systems with their attendant disadvantages in no way is meant to infer that the present invention excludes such materials, methods, and systems. Indeed, certain embodiments of the invention may solve some of the aforementioned disadvantages, yet utilize the same or similar materials, methods and/or systems.

SUMMARY OF THE INVENTION

It would be desirable to provide an apparatus and method for forming tow-based absorbent structures, such as absorbent cores, that have only a single tissue sheet that encases the entire absorbent core structure. It would further be desirable for such an apparatus and method to be efficient, easy to operate, and capable of operating at high line speeds. In accordance with these and other features of various embodiments of the invention, there is provided an apparatus and method for forming tow-based absorbent cores having a single casing sheet.

In accordance with one embodiment of the invention, there is provided an apparatus having a tow supply mechanism for providing tow material, a particulate matter supply mechanism for providing particulate matter, a casing sheet supply mechanism for providing casing sheet material, and a vacuum draw roll positioned to combined the tow, particulate matter and casing sheet into and open core composite supply. The vacuum draw roll has a foraminous center surface having a width defined by a first edge and a second edge, and the vacuum draw roll is rotatable about a first axis. In addition, one or more angled surfaces are provided and positioned to create one or more obtuse angles in the open core composite supply, and one or more folders are provided to further fold the one or more obtuse angles in the open core composite supply to form a folded core composite supply.

In accordance with another embodiment of the invention, there is provided an apparatus for forming absorbent structures having a single casing sheet, that has a casing sheet supply mechanism for providing casing sheet material, a tow supply mechanism for providing tow material, and a particulate matter supply mechanism for providing particulate matter. In this embodiment, the particulate matter supply mechanism is positioned to deposit the particulate matter onto the casing sheet material. In this embodiment the apparatus has a vacuum draw roll having a foraminous center surface, the foraminous center surface having a width defined by a first edge and a second edge and being rotatable about a first axis. The vacuum draw roll is positioned after the particulate matter supply mechanism to deposit the tow material onto the casing sheet material to form a open core composite supply. In addition, this embodiment has one or more folders to fold the open core composite supply into a folded core composite supply.

In various embodiments of the invention, the tow material is cellulose acetate, the particulate matter is superabsorbent particles, and the casing sheet materials is tissue. In other embodiments, the particulate matter supply mechanism is a vibratory feeder and the tow supply mechanism is a tow forming jet.

In yet another embodiment, the casing sheet material has a center region and first and second side regions located on opposite sides of the center region. The first side region extends from a first side of the center region to a first edge of the casing sheet material, and the second side region extends from a second side of the center region to a second edge of the casing sheet material. In this embodiment, the casing sheet material is wider than the tow material, the tow material is positioned adjacent to the center region of the casing sheet material in the open core composite supply, and the one or more angled surfaces are positioned to create a first obtuse angle at or near to the first side of the center region, and a second obtuse angle at or near the second side of the center region. Adhesive applicators may be used in these or other embodiments of the invention. In one embodiment, a first adhesive applicator is positioned before the vacuum draw roll to apply adhesive to the center region of the casing sheet material. In another embodiment, a second adhesive applicator is operatively associated with the one or more folders and positioned to apply adhesive to at least one of the first and second side regions of the casing sheet material.

In still other embodiments, the angled surfaces may be operatively associated with the vacuum draw roll, and may comprise first and second tapering surfaces that extend from respective edges of the foraminous center surface and taper inward from the center surface towards the axis about which the vacuum draw roll rotates.

In another embodiment, the invention may have a break drum positioned between the vacuum draw roll and the one or more folders. The break drum is rotatable about a second axis and has a center surface that has a width defined by a third edge and a fourth edge. The one or more angled surfaces may, in one embodiment, be operatively associated with the break drum, and may be first and second tapering surfaces, that extending from respective edges of the center surface of the break drum and taper inward from the center surface towards the axis about which the break drum rotates.

In another embodiment, the invention includes an open core composite supply conveyor that is positioned to convey the open core composite supply from the vacuum draw roll to the one or more folders. The open core composite supply conveyor may have an arcuate region substantially adjacent to a sector of the vacuum draw roll.

In still another embodiment, the vacuum draw roll of the invention may have a rotatable outer drum upon which the foraminous center surface is disposed, and an inner structure disposed at least partially within the rotatable outer drum. In such an embodiment, the one or more angled surfaces may be first and second tapering surfaces, located on the outer drum, that extend from respective edges of the foraminous center surface and taper inward towards the first axis. The inner structure has a vacuum chamber having one or more vacuum passages forming a vacuum zone subadjacent at least a portion of the foraminous center surface. The vacuum zone may have a leading edge and a trailing edge, as located relative to the direction of rotation of the rotatable outer drum, and a positive air blow-off port located at the trailing edge of the vacuum zone.

In yet another embodiment, the foraminous center surface of the vacuum draw roll may have a central vacuum region and first and second lateral vacuum regions, that are located between the central vacuum region and the edges of the foraminous center surface. In this embodiment, the central vacuum region may be recessed. In this embodiment, the tow material may have an average width approximately equal to or less than a width of the central vacuum region, and the central vacuum region may be positioned to receive substantially the entire width of the tow material. The first and second lateral vacuum regions also may be positioned to apply a vacuum to the casing sheet material.

In still another embodiment, the present invention provides a method for preparing absorbent structures that have a single casing sheet. In one embodiment, the method involves providing tow material, providing particulate matter, providing casing sheet material, and forming an open core composite supply by combining the tow material, the particulate matter and the casing sheet material on a vacuum draw roll comprising a foraminous center surface, the foraminous center surface having a width defined by a first edge and a second edge and being rotatable about a first axis. This method also includes creating one or more obtuse angles in the open core composite supply using one or more angled surfaces and, forming a folded core composite supply by folding flat the one or more obtuse angles in the open core composite supply. In one embodiment of the method, the open core composite supply may be formed at the same time that the one or more obtuse angles are formed in it. In various other embodiments the method may further employ the various embodiments of the apparatus described immediately above.

These and other features of the invention will be readily apparent from the Detailed Description that follows, along with reference to the drawings appended hereto.

DETAILED DESCRIPTION OF THE PREFERRED EMBODIMENTS

Figure 1:
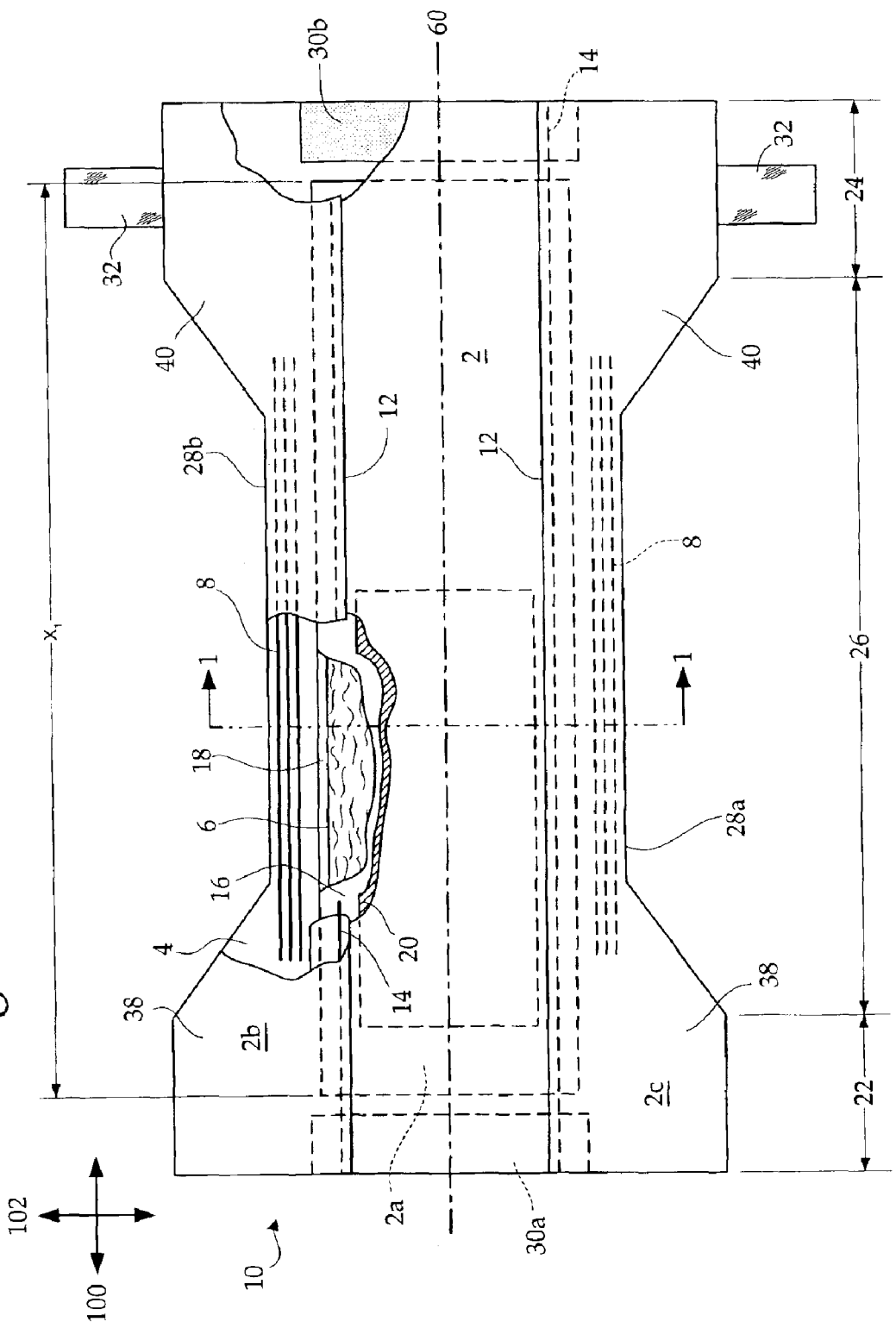
FIG. 1 is a plan view of a diaper-type absorbent garment, shown with the effects of elastics removed for clarity.

As used herein, the term "absorbent garment" or "garment" refers to garments that absorb and contain exudates, and more specifically, refers to garments that are placed against or in proximity to the body of the wearer to absorb and contain the various exudates discharged from the body. A non-exhaustive list of examples of absorbent garments includes diapers, diaper covers, disposable diapers, training pants, feminine hygiene products and adult incontinence products. The term garment includes all variations of absorbent garments, including disposable absorbent garments that are intended to be discarded or partially discarded after a single use (i.e., they are not intended to be laundered or otherwise restored or reused) and unitary disposable absorbent garments that have essentially a single structure (i.e., do not require separate manipulative parts such as a diaper cover and insert). As used herein, the term "diaper" refers to an absorbent garment generally worn by infants and incontinent persons about the lower torso.

The claims are intended to cover all of the foregoing classes of absorbent garments, without limitation, whether disposable, unitary or otherwise. The invention will also be understood to encompass, without limitation, all other types of absorbent structure that may comprise an absorbent core, whether described herein or not. Preferably, the absorbent core or the garment is thin in order to improve the comfort and appearance of a garment. The importance of thin, comfortable garments is disclosed, for example, in U.S. Pat. No. 5,098,423 to Pieniak et al., which is incorporated herein by reference in its entirety and in a manner consistent with the present invention.

Absorbent garments and diapers may have a number of different constructions. In each of these constructions it is generally the case that an absorbent core is disposed between a liquid pervious, body-facing topsheet, and a liquid impervious, exterior facing backsheet. In some cases, one or both of the topsheet and backsheet may be shaped to form a pant-like garment. In other cases, the topsheet, backsheet and absorbent core may be formed as a discrete assembly that is placed on a main chassis layer and the chassis layer is shaped to form a pant-like garment. The garment may be provided to the consumer in the fully assembled pant-like shape, or may be partially pant-like and require the consumer to take the final steps necessary to form the final pant-like shape. In the case of training pant-type garments and most adult incontinent products, the garment is provided fully formed with factory-made side seams and the garment is donned by pulling it up the wearer's legs. In the case of diapers, a caregiver usually wraps the diaper around the wearer's waist and joins the side seams manually by attaching one or more adhesive or mechanical tabs, thereby forming a pant-like structure. For clarity, the present invention is described herein only with reference to a diaper-type garment in which the topsheet, backsheet and absorbent core are assembled into a structure that forms a pant-like garment when secured on a wearer using fastening devices, although the invention may be used with other constructions.

Throughout this description, the expressions "upper layer," "lower layer," "above" and "below," which refer to the various components included in the absorbent garments of the invention (including the layers surrounding the absorbent core units), as well as the depiction in the drawings of certain layers or materials that are "above" or "below" one another, are used merely to describe the spatial relationship between the respective components. The upper layer or component "above" the other component need not always remain vertically above the core or component, and the lower layer or component "below" the other component need not always remain vertically below the core or component. Indeed, embodiments of the invention include various configurations whereby the core may be folded in such a manner that the upper layer ultimately becomes the vertically highest and vertically lowest layer at the same time. Other configurations are contemplated within the context of the present invention.

The term "component" can refer, but is not limited, to designated selected regions, such as edges, corners, sides or the like; structural members, such as elastic strips, absorbent pads, stretchable layers or panels, layers of material, or the like; or a graphic, embossed pattern, or the like.

Throughout this description, the term "disposed" and the expressions "disposed on," "disposing on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the terms "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core of either the top sheet or the back sheet.

Throughout this description, the expression "fibrous material" denotes any fibrous material that may be used in an absorbent garment, including without limitation, various hardwood and softwood fluff pulps, tissues, cottons, and any other fibrous materials described herein. "Fibrous material" used in the context of the present invention is not intended to limit the invention to any particular type of fibrous material.

Throughout this description, the expression "tow fibers" relates in general to any continuous fiber. Tow fibers typically are used in the manufacture of staple fibers, and preferably are comprised of synthetic thermoplastic polymers. Usually, numerous filaments are produced by melt extrusion of the molten polymer through a multi-orifice spinneret during manufacture of staple fibers from synthetic thermoplastic polymers in order that reasonably high productivity may be achieved. The groups of filaments from a plurality of spinnerets typically are combined into a tow which is then subjected to a drawing operation to impart the desired physical properties to the filaments comprising the tow.

A preferred embodiment of the present invention comprises a disposable absorbent garment 10 of the diaper type, such as shown, for example, in FIG. 1. It should be understood, however, that the present invention is applicable to other types of absorbent garments. With reference to FIG. 1, the diaper 10 according to a first preferred embodiment is shown in a relaxed condition with the effects of the elastics removed for purposes of clarity in the description. The diaper 10 has a generally hourglass shape and can generally be defined in terms of a front waist region 22, a back waist region 24, and a crotch region 26. Those skilled in the art will recognize that "front" and "back" are relative terms, and these regions may be transposed without departing from the scope of the present invention. Alternatively, the diaper can be configured in a generally rectangular shape or in a "T" shape. A pair of leg openings 28a, 28b extend along at least a portion of the crotch region 26. The diaper preferably comprises a topsheet 2, a backsheet 4, which may be substantially coterminous with the topsheet 2, and an absorbent core 6 disposed between at least a portion of the topsheet 2 and backsheet 4. One or more pairs of leg elastics 8 (three pairs are shown in FIG. 1) may be disposed to extend adjacent to leg openings 28a, 28b, respectively. Of course, in other embodiments, the leg elastics 8 may be omitted altogether.

The diaper may further include a front waist elastic system 30a, a back waist elastic system 30b, a fastening system 32 (e.g., tape or other suitable mechanical fastener) and a waste containment system in the form of waste containment flaps 12 (also known as standing leg gathers). Waste containment flaps 12 (FIG. 2) preferably extend from the front waist region 22 to the back waist region 24 along opposite sides of a longitudinal center line or axial center line 60 of the diaper 10, or alternatively only along a portion thereof. The front waist region 22 and rear waist region 24 may include ear portions 38,40 extending outwardly from the leg openings 28a, 28b.

A variety of backsheet and topsheet constructions and materials are available and known in the art, and the invention is not intended to be limited to any specific materials or constructions of these components. The backsheet 4 is of any suitable pliable liquid-impervious material known in the art. Typical backsheet materials include films of polyethylene, polypropylene, polyester, nylon, and polyvinyl chloride and blends of these materials. For example, the backsheet can be a pigmented polyethylene film having a thickness in the range of 0.02–0.04 mm. The moisture-pervious topsheet 2 can be any suitable relatively liquid-pervious material known in the art that permits passage of liquid therethrough. Non-woven topsheet materials are exemplary because such materials readily allow the passage of liquids to the underlying absorbent core 6. Examples of suitable topsheet materials include non-woven spunbond or carded webs of polypropylene, polyethylene, nylon, polyester and blends of these materials.

The backsheet 4 and the topsheet 2 preferably are "associated" with one another. The term "associated" encompasses configurations whereby the topsheet 2 is directly joined to the backsheet 4 by affixing the topsheet 2 directly to the backsheet 4, and configurations whereby the topsheet 2 is indirectly joined to the backsheet 4 by affixing the topsheet 2 to intermediate members which in turn are affixed to the backsheet 4. While the backsheet 4 and topsheet 2 in the preferred embodiment have substantially the same dimensions, they may also have different dimensions.

In addition, the backsheet 4 may be covered with a fibrous, nonwoven fabric such as is disclosed for example in U.S. Pat. No. 4,646,362, which is incorporated herein by reference in its entirety and in a manner consistent with the present invention. Materials for such a fibrous outer liner include a spun-bonded nonwoven web of synthetic fibers such as polypropylene, polyethylene or polyester fibers; a nonwoven web of cellulostic fibers, textile fibers such as rayon fibers, cotton and the like, or a blend of cellulostic and textile fibers; a spun-bonded nonwoven web of synthetic fibers such as polypropylene; polyethylene or polyester fibers mixed with cellulostic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulostic, pulp or textile fibers.

The backsheet 4 may comprise multiple panels, such as three panels wherein a central poly backsheet panel is positioned adjacent the absorbent core while outboard nonwoven breathable side backsheet panels are attached to the side edges of the central poly backsheet panel. The backsheet may also be formed from microporous poly coverstock for added breathability. In other embodiments, the backsheet may be a laminate of several sheets. The backsheet may further be treated to render it hydrophilic or hydrophobic, and may have one or more visual indicators associated with it, such as labels indicating the front or back of the diaper or other characters or colorations. The present invention is not limited to any particular backsheet 4 material or construction.

The topsheet 2 may be formed from one or more panels of material and may comprise a laminated sheet construction. In the embodiment of FIG. 1, the topsheet comprises three separate portions or panels. A three-panel topsheet may comprise a central topsheet panel 2a (FIG. 2) that preferably is formed from a liquid-pervious material that is either hydrophobic or hydrophilic. The central topsheet panel 2a may be made from any number of materials, including synthetic fibers (e.g., polypropylene or polyester fibers), natural fibers (e.g., wood or cellulose), apertured plastic films, reticulated foams and porous foams to name a few. One preferred material for a central topsheet panel 2a is a cover stock of single ply non-woven material which may be made of carded fibers, either adhesively or thermally bonded, perforated plastic film, spunbonded fibers, or water entangled fibers, which generally weigh from 0.3–0.7 oz./yd$^2$ and have appropriate and effective machine direction and cross-machine direction strength suitable for use as a baby diaper cover stock material, as are known in the art. The central topsheet panel 2a preferably extends from substantially the front waist region 22 to the back waist region 24 or a portion thereof.

The second and third topsheet panels 2b, 2c in this embodiment may be positioned laterally outside of the central topsheet panel 2a. The outer topsheet panels 2b, 2c preferably are substantially liquid-impervious and hydrophobic, preferably at least in the crotch area. The outer edges of the outer topsheet panels may substantially follow the corresponding outer perimeter of the backsheet 4. The material for the outer topsheet portions or panels preferably is polypropylene and can be woven, non-woven, spunbonded, carded or the like, depending on the application.

An inner region 34 (FIG. 2) of the outer topsheet portions or panels 2b, 2c preferably is attached by, e.g., an adhesive, to the outer edges 36 of the inner topsheet portion or panel 2a. At the point of connection with the outer edges 36 of the inner topsheet portion or panel 2a, the inner regions 34 of the outer topsheet portions or panels 2b, 2c extend upwardly to form waste containment flaps 12. The waste containment flaps 12 may be formed of the same material as the outer topsheet portions or panels 2b, 2c, as in the embodiment shown. The waste containment flaps 12 may also be formed from separate elasticized strips of material that are associated with the topsheet, backsheet or both, or otherwise integrated into the garment.

The waste containment flaps 12 may be treated with a suitable surfactant to modify their hydrophobicity/hydrophilicity or imbue them with skin wellness products as desired. The central topsheet portion or panel 2a may extend past the connection point with the waste containment flaps 12 and even extend to the periphery of the backsheet. Still further, the central topsheet portion or panel 2a could extend fully between the outer topsheet portions or panels 2b, 2c and even beyond so that the outer edges 36 of the central topsheet portion or panel 2a are coextensive with and sandwiched between the outer topsheet portions or panels 2b, 2c and the backsheet 4.

The waste containment flaps 12 each preferably includes a portion that folds over onto itself to form an enclosure. One or more elastic members 14 (FIG. 2) may be secured in the enclosure in a stretched condition. As has been known at least as long the disclosure of Tetsujiro, Japanese Patent document 40-11543, when the flap elastic 14 attempts to assume the relaxed, unstretched condition, the waste containment flaps 12 rise above the surface of the central topsheet portion or panel 2a. Various other configurations of topsheets 2 and waste containment systems, such as flaps 12, are known in the art, and the present invention is not intended to be limited to any particular design for these components.

The waist elastics 30a, 30b (FIG. 1) may be similar structures or different to impart similar or different elastic characteristics to the front and back waist portions 22, 24 of the diaper. In general, the waist elastics may comprise elastically extensible foam strips positioned at the front and back waist sections 22, 24. The foam strips are preferably about 0.50 inches to about 1.50 inches wide and about 3 inches to about 6 inches long. The foam strips are preferably positioned between the topsheet portions or panels and the backsheet 4. Alternatively, a plurality of elastic strands may be employed as waist elastics rather than foam strips. The foam strips are preferably polyurethane, but could be any other suitable material that preferably decreases waist band roll over, reduces leakage over the waist ends of the absorbent garment, and generally improves comfort and fit. The front and back waist foam strips 30a, 30b are stretched 50–150%, preferably 100% before being adhesively secured between the backsheet 4 and topsheet 2. Waist elastics are known in the art, and the present invention is not limited to the use of a particular waist elastic system, or to the inclusion of waist elastics at all.

Each leg opening 28a, 28b may be provided with a leg elastic containment system 8, sometimes referred to as conventional leg gathers. In a preferred embodiment, three strands of elastic threads are positioned to extend adjacent the leg openings 28a, 28b between the outer topsheet portions or panels 2b, 2c and the backsheet 4 the selection of appropriate elastics and the construction of leg elastic containment systems is known in the art. For example, the leg elastics 8 may be ultrasonically bonded, heat/pressure sealed using a variety of bonding patterns, or glued to the diaper 10.

Various commercially available materials may be used for the leg elastics 8 and elastic members 14, such as natural rubber, butyl rubber or other synthetic rubber, urethane, elastomeric materials such as spandex, which is marketed under various names, including LYCRA (DuPont), GLOSPAN (Globe) and SYSTEM 7000 (Fulflex), and so on. The present invention is not limited to any particular elastic.

The fastening system of the diaper 10 may be attached to the back waist region 24, and preferably comprises tape tabs or mechanical fasteners 32. However, any fastening known in the art will be acceptable. Moreover, the fastening system may include a reinforcement patch below the front waist portion so that the diaper may be checked for soiling without compromising the ability to reuse the fastener. Alternatively, other diaper fastening systems are also possible, including safety pins, buttons, and snaps. Fastening systems are known in the art, and the present invention is not limited to using any particular fastening, and may be constructed without any fastening system at all, such as in training pant-type garments.

As stated previously, the invention has been described in connection with a diaper. The invention, however, is not intended to be limited to application only in diapers. Specifically, the present invention may be readily adapted for use in other absorbent garments besides diapers, including, but not limited to, training pants, feminine hygiene products and adult incontinence products.

Figure 2:
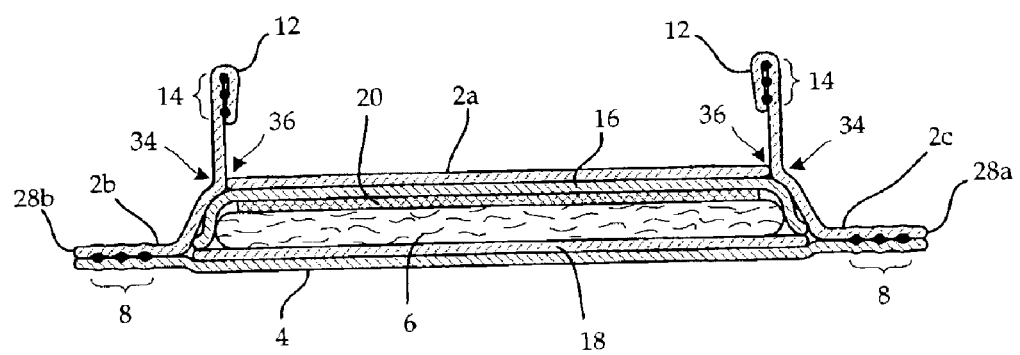
FIG. 2 is a cross-sectional view of the garment of FIG. 1, as viewed from reference line 1—1.

The underlying structure beneath the topsheet 2 may include, depending on the diaper construction, various combinations of elements, but in each embodiment, it is contemplated that the absorbent garment will preferably include an absorbent core 6. For example, an additional layer 20 may be disposed between the topsheet 2 and absorbent core 6, as shown in FIG. 2, and/or other additional layers may be disposed between these layers, or between absorbent core 6 and backsheet 4. The additional layer 20 or layers may comprise any useful layer known in the art or developed hereafter, such as a fluid acquisition layer, a distribution layer, an additional fibrous layer optionally containing SAP, a wicking layer, a storage layer, or combinations and fragments of these layers. Such layers may be provided to assist with transferring fluids to the absorbent core 6, handling fluid surges, preventing rewet, containing absorbent material, improving core stability, or for other purposes. Skilled artisans are familiar with the various additional layers that may be included in an absorbent article, and the present invention is not intended to be limited to any particular type of materials used for those layers. Rather, the invention encompasses all types of wicking layers, all types of distribution layers, etc., to the extent that type of layer 20 is utilized.

The dimensions of additional layer(s) 20 may be the same as or different from the dimensions of the absorbent core 6 and/or topsheet 2 and backsheet 4. It is preferred that additional layer(s) 20 have a width in the lateral direction (102) of anywhere from about 10 mm to about 100 mm, and preferably from about 25 mm to about 80 mm.

Although the absorbent core 6 depicted in FIG. 1 has a substantially rectangular shape as viewed in the plan view, other shapes may be used, such as a "T" shape or an hourglass shape. The absorbent core 6 may extend into either or both of the front and back waist regions 24, 22. The shape and construction of the absorbent core 6 may be selected to provide the greatest absorbency in target areas where body fluids are most likely to strike the diaper 10, which is often referred to as zoned absorbency. The absorbent core 6 may also comprise a number of layers of similar or different construction. The absorbent core may be associated with the topsheet 2, backsheet 4, or any other suitable part of the garment 10 by any method known in the art, in order to fix the absorbent core 6 in place.

Generally, in a preferred embodiment, the absorbent core 6 comprises particles of super absorbent polymer distributed within a fibrous structure. Additional fibrous or particulate additives may be disposed within the absorbent core 6 to add to the core's strength and SAP efficiency or to otherwise enhance the performance of the garment. The absorbent core 6 may be partially or wholly surrounded by a tissue layer 16, 18, and other additional layers 20 may be added to provide further benefits. The various components of the absorbent core 6 are now described in greater detail.

Certain fibrous materials preferably are used to form the fibrous structure of the absorbent core 6 of the present invention. These fibrous materials maintain high SAP efficiencies when the SAP weight concentration is in the range of about 50–95%, more preferably about 65–95%, and most preferably about 80–95% (as measured in the absence of tissue, glue or other core components). For example, the fibrous structure of the absorbent core 6 may be made with cellulose acetate fibers, polypropylene fibers, rayon fibers, Courtauld's LYOCELL fibers, polyacrylonitrile fibers, surface-modified (hydrophilic) polyester fibers, surface-modified polyolefin/polyester bicomponent fibers, surface-modified polyester/polyester bicomponent fibers, cotton fibers, blends of the foregoing materials, and the like.

Of the foregoing, cellulose acetate or polyolefinic (e.g., polypropylene or polyethylene) tow fibers are the most preferred materials for use as the fibrous structure. In addition, rayon, Courtauld's LYOCELL, polyacrylonitrile, cotton fibers and cotton linters have similar properties to cellulose acetate and are alternatively preferred. The remaining fibers, surface-modified polyolefin/polyester bicomponent fibers, and surface-modified polyester/polyester bicomponent fibers are also believed to be effective as a fibrous structure or as fibrous additives. Of course, other fibers may also be used. To maintain high SAP concentrations, the weight concentration of fibrous material forming the absorbent core 6 of the invention preferably is about 5–50%, more preferably about 5–35%, and most preferably about 5–20% (as measured in the absence of tissue, glue or other core components). Most preferably, the absorbent core 6 comprises from about 80–95% SAP and from about 5–20% fibrous structure material chosen from the foregoing group.

In accordance with the present invention, improved absorbent articles are advantageously based upon continuous crimped filament tow, and accordingly, the central fibrous structure of the core 6 is advantageously prepared therefrom. This fiber structure has high structural integrity, and as such, is distinct from a matrix of discontinuous fibers, often described as fluff or fluff pulp, that is commonly used in the prior art. The high structural integrity enables the production of stronger webs than those formed from discontinuous fibers, which in turn are believed to enable the production of thinner absorbent pads. In addition, the use of such fibers enables the production of ultra low density absorbent cores, when compared to absorbent cores prepared by dispersing SAP particles in fluff. The reduction in density is largely attributable to the reduced weight of the fibrous structure. Absorbent cores 6 constructed from a blend of such materials and SAP are referred to herein as "tow/SAP" cores or "tow-based" cores.

Beneficially, cellulose ester tow is used to form the fibrous structure. Non-limiting examples of suitable cellulose esters include cellulose acetate, cellulose propionate, cellulose butyrate, cellulose caproate, cellulose caprylate, cellulose stearate, highly acetylated derivatives thereof such as cellulose diacetate, cellulose triacetate and cellulose tricaproate, and mixtures thereof such as cellulose acetate butyrate. A suitable cellulose ester preferably will have the ability to absorb moisture, is biodegradable, and is influenced not only by the substituent groups but also by the degree of substitution. The relationship between substituent groups, degree of substitution and biodegradability is discussed in W. G. Glasser et al, BIOTECHNOLOGY PROGRESS, vol. 10, pp. 214–219 (1994), the disclosure of which is incorporated herein by reference in its entirety.

Alternatively, a polyolefinic fiber tow may be used beneficially with the present invention. Polyolefinic fibers offer certain advantages, for example, they are typically available in a wider denier range than other materials and they are thermoplastic and thus can be embossed. In addition, polyolefinic fibers have a relatively high resiliency, making more able to spring back after being placed under pressure. Such resiliency is beneficial because it creates a buffer between the wearer and the wetted SAP that reduces rewet values and makes the garment more comfortable.

Typically, the denier per fiber (dpf) of the tow fiber will be in the range of about 1 to 30, preferably about 7 to 15, and most preferably about 10. For the same weight product, filaments of lower dpf may provide increased surface area and increased moisture absorption. Total denier of the tow may vary within the range of about 5,000 to 80,000, depending upon the process and material used, and is preferably about 30,000. Lower total deniers provide a more open structure that allows free transfer of fluid, while higher total deniers tend to obstruct the movement of fluid and rely more on capillary fluid conveyance. The total denier should not be excessively reduced, however, as this may result in inadequate core strength, reduced resiliency (leading to increased rewet), and reduced comfort. The foregoing dpfs and total deniers are beneficial for cellulose acetate tows and polyolefinic fiber tows. Of course, other dpfs and total deniers may be selected according to the particular material used for the fiber. The fibers may have a circular, ovate, rectilinear, or any other cross section. In one embodiment, the fibers have a tri-lobal cross section with an area of about $3.36 \times 10^{-6}$ cm$^2$. Such a cross-sectional shape may provide improved bending stiffness, increased wicking, or other beneficial properties.

Tow typically is provided as a relatively dense matrix of fibers, and it is often desirable to "open" (also known as "fluffing" or "blooming") the tow into a more voluminous cotton-like matrix. Various methods and devices for opening tow are known in the art. For example, U.S. Pat. No. 4,468,845 to Harris discloses a tow forming jet having a jet portion that injects gasses into the tow that cause the tow to separate when the gasses escape, and a bustle portion that collects the tow into a cotton-like mass, thereby essentially completing the blooming operation. Another device, disclosed in U.S. Pat. No. 6,253,431, operates without a dancer (i.e. tension plate). These or any other tow opening device may be used with the present invention.

Tow having crimped filaments may be used with the present invention, as the crimps aid with opening the tow. The separation of filaments resulting from the opening process advantageously results in increased available filament surface area for superabsorbent material immobilization and increased moisture absorption. Gel blocking also may be reduced by using crimped tow in the absorbent core 6. As therefore may be understood, more crimp is typically better, with an excess of about 20 crimps per inch being usually preferred. Continuous filament cellulose ester tow having crimped filaments with about 25 to 40 crimps per inch is commercially available from Hoechst Celanese Corporation of Charlotte, N.C. However, it should be understood that uncrimped tow filaments or filaments having relatively few crimps also may be used with the present invention, and may provide a cost advantage without substantially reducing the performance of the garment.

If desired, an absorbent core 6 of multiple layer thickness may be provided. To this end, the tow may be, for example, lapped or crosslapped in accordance with conventional procedures. In this way, a superabsorbent, absorptive material of a desired weight and/or thickness may be provided. The specific weight or thickness will depend upon factors including the particular end use.

Any superabsorbent polymer (SAP) now known or later discovered may be used in the absorbent core 6, so long as it is capable of absorbing liquids. In addition, the SAP may be omitted from the core 6 in some circumstances, such as when a swim garment is produced. Useful SAP materials are those that generally are water-insoluble but water-swellable polymeric substances capable of absorbing water in an amount that is at least ten times the weight of the substance in its dry form. In one type of SAP, the particles or fibers may be described chemically as having a back bone of natural or synthetic polymers with hydrophilic groups or polymers containing hydrophilic groups being chemically bonded to the back bone or in intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Also included are water swellable polymers of water soluble acrylic or vinyl monomers crosslinked with a polyfunctional reactant. Such modified polymers may also be crosslinked to reduce their water-solubility, and such cross-linked SAPs have been found to provide superior performance in some absorbent cores. A more detailed recitation of superabsorbent polymers is found in U.S. Pat. No. 4,990,541 to Nielsen, the disclosure of which is incorporated herein by reference in its entirety. The SAP is preferably selected to provide high absorbency performance for the particular application. The measure of the SAP's absorbency performance may be evaluated in a number of ways, as will be understood by those skilled in the art. For example, it may be desirable, in some cases, to provide a SAP having a high measure of saline flow conductivity (SFC), as is described in U.S. Pat. No. 5,562,646 to Goldman et. al, which is incorporated herein by reference in its entirety and in a manner consistent with the present invention. However, the present invention is also suitable for providing a low saline flow conductivity, which also may provide certain benefits, such as higher capacity and absorbency under load. Of course, the SAP may be selected to provide other properties or combinations of properties as well.

Commercially available SAPs include a starch modified superabsorbent polymer available under the trade name SANWET from BASF of Portsmouth, Va. SANWET is a starch grafted polyacrylate sodium salt. Other commercially available SAPs include a superabsorbent derived from polypropenoic acid, available under the trade name DRYTECH 520 SUPERABSORBENT POLYMER from The Dow Chemical Company, Midland Mich.; AQUA KEEP manufactured by Seitetsu Kagaku Co., Ltd.; ARASORB manufactured by Arakawa Chemical (U.S.A.) Inc.; and FAVOR manufactured by Stockhausen Inc. Still other commercially available SAPs include SA55SX, available from Sumitomo Chemical Co. Ltd. of Osaka, Japan, and 3900, 8400 and 8600 provided by BASF of Portsmouth, Va.

The SAP may be provided in any particle size, and suitable particle sizes vary greatly depending on the ultimate properties desired. Preferably, a fine particulate rather than a coarse particulate, is used in the invention, and preferably a fine particulate that passes through an about 200 mesh screen is used.

It has been known to prepare absorbent cores comprised of cellulose acetate tow or other polymeric fibers and SAP, as described in U.S. Statutory Invention Registration H1565, and U.S. Pat. Nos. 5,436,066, and 5,350,370, the disclosures of each of which are incorporated by reference herein in their entirety and in a manner consistent with the present invention. It was conventional to add tackifying agents, specific size fibers, or specific fibers in combination with fluff, in order to prepare the absorbent core and immobilize the SAP particles. These additional materials may add to density of the core, or otherwise adversely affect the overall performance of the absorbent garment made therefrom. Thus, the use of such additives (or any other additives, adhesives, bonding agents or the like) should be controlled to minimize any negative effects caused by their inclusion.

The total basis weight of the absorbent core 6 including fibrous materials, SAP, tissue, additional layers, and additives, typically may be anywhere from about 50 grams per square meter (gsm) to about 1,000 gsm. The most preferred total basis weight of the absorbent core 6 is about 250 gsm to about 700 gsm.

Additional particles or fibrous additives may be added to the absorbent core 6 to help maintain high SAP efficiency, to reduce the cost of the garment, or to provide other benefits. Fibrous additives may be introduced as part of the supply of unopened tow or may be added to tow after it has been opened. In a preferred embodiment, particulate additives generally may be added to the tow after it has been opened to allow practical manufacture of the tow and to prevent losses of the particulate additives during processing.

In one embodiment, about 1–10%, and preferably about 5%, by weight of thermally bondable synthetic fibers may be added to the absorbent core 6 to impart additional wet strength to the laminate. These additive fibers may improve the stability of the core during use of the diaper. The preferred synthetic fibers for such an embodiment are polyolefin/polyester fibers and polyester/polyester bicomponent fibers.

In another embodiment, the fibrous structure may comprise a combination of preferred tow materials or a combination of a tow material and a fluff pulp material, such as a blend of cellulose ester and conventional soft or hard wood fibers. Such combinations may be useful to maintain the improved SAP efficiency available from the crimped filament tow-based fibrous structure while providing additional benefits. For example, it has been discovered that an absorbent core 6 having a 150 g/m² composite comprised of 80% SAP, 10% cellulose acetate, and 10% conventional fluff pulp has a SAP efficiency of about 85%, whereas an absorbent core 6 comprised of 80% SAP and 20% fluff pulp SAP has an efficiency of about 70%.

The particulate additives that may be added to the absorbent core 6 preferably are insoluble, hydrophilic polymers with particle diameters of 100 μm or less. These particulate additives may be chosen to impart optimal separation of the SAP particles. Examples of preferred particulate additive materials include, but are not limited to, potato, corn, wheat, and rice starches. Partially cooked or chemically modified (i.e., modifying hydrophobicity, hydrophilicity, softness, and hardness) starches can also be effective. Most preferably, the particulate additives comprise partially cooked corn or wheat starch because in this state, the corn or wheat are rendered larger than uncooked starch and in the cooked state remain harder than even swollen SAP. In any event, regardless of the particulate additive chosen, one of the many important criteria is to use particulate additives that are hard hydrophilic materials relative to swollen SAP or which are organic or inorganic polymeric materials about 100 microns in diameter. Fibrous and particulate additives can be used together in these absorbent laminates. Examples of SAP/particulate and SAP/fiber/particulate additives include those described in, for example, U.S. Pat. No. 6,068,620.

Other particulate or powdered additives also may be deposited within the absorbent core 6 to provide odor control, skin wellness, and improved appearance. For example, zeolites, sodium bicarbonate and perfumes may be added to reduce or mask odors, and titanium dioxide or other color-imbuing compounds may be added to provide the absorbent core 6 with a more pleasant color.

The absorbent core 6 preferably comprises a tissue wrapping that at least partially encloses the preferred blended tow and SAP, such as disclosed in U.S. Pat. No. 6,068,620. The tissue wrapping is useful, for example, for containing the SAP within the absorbent core 6 and providing strength to the core during manufacturing and use. In a preferred embodiment, the tissue wrapping comprises first and second tissue layers 16, 18 that encase the absorbent core 6, and may optionally also encase one or more additional layers 20. Preferably, the first tissue layer 16 is located generally between the topsheet 2 and the absorbent core 6, and is hydrophilic and fluid pervious. It is also preferred that the second tissue layer 18 be located between the backsheet 4 and the absorbent core 6 and be hydrophobic and fluid impervious. The tissue wrapping may also comprise a single tissue layer that has been folded to encase the absorbent core, and that may be zone treated to render the portion that forms the lower tissue layer 18 hydrophobic and fluid impervious. Embodiments having a single tissue layer are described in more detail below, but generally may have all of the features described herein with reference to embodiments having multiple tissue layers. The tissue layers 16, 18 or the whole core 6 may be crimped, folded, sealed or bonded to help contain the SAP particles.

In one embodiment, the tissue, fibrous structure and SAP of the absorbent core may be adhesively or thermally bonded to improve the absorbent core's wet strength and core stability. This may, in some cases, result in slower than adequate rates of absorption and poor SAP efficiency. In another embodiment the SAP and fibrous structure may be hydrogen bonded to additional the tissue layers 16, 18. When a tow-based fibrous structure having a high concentration of SAP is hydrogen bonded to first and second tissue layers 16, 18 to form an absorbent core 6, the SAP efficiency is not impaired, wet strength increases, and the first and second tissue layers 16, 18 add stability to the core 6 during manufacture. It has been found that when the fibrous structure of the absorbent core 6 is hydrogen bonded using water to the tissue layers 16, 18, unexpectedly good "core utilization" is realized. "Core utilization" is the percentage of the total capacity of a core that can be absorbed in a demand absorbency test. This unexpected performance improvement is believed to be the result of the beneficial liquid distribution provided by the intimate bond between the fibers of the fibrous structure and the tissue layers 16, 18.

In another preferred embodiment, the first and second tissue layers 16, 18 are coated with adhesive prior to being placed on either side of the absorbent core 6, thereby providing strength to the core and adhesively holding a portion of the SAP in place during use. The tissue layers 16, 18 may be provided having a width greater than the fibrous structure of the absorbent core 6, and the portions of the tissue layers 16, 18 extending past either side of the fibrous structure of the core 6 may be bonded to one another to provide further SAP retention capability. In still another embodiment, if the fibrous structure contains about 1–5% by weight thermally bondable synthetic fibers, bonding to the tissue layers 16, 18 may be achieved using thermal bonds.

The absorbent core 6 of the present invention may flat or folded when it is fixed in place between the topsheet 2 and backsheet 4. Folded cores may provide additional performance benefits, such as improved fluid redistribution, greater SAP efficiency, and so on. The absorbent core 6 can be folded in any suitable manner, including any and all of those disclosed in U.S. Pat. No. 6,068,620. Those skilled in the art will appreciate that the absorbent core 6 can be folded such that the adjacent sides are touching one another, or so that channels are formed in certain areas. For example, the absorbent core 6 can be folded in the form of a "C" where the curled ends may be spaced apart to form a channel there between, and the lower edges of the curled ends may be disposed adjacent the upper edges of the bottom portion of the folded article. Alternatively, another absorbent material, or another absorbent core 6 may be disposed in the space formed by the standard "C" fold. The same considerations may be given to embodiments having a "G" fold or a "U" fold where the spaces formed by these folds may be filled with another absorbent material, another absorbent core 6, left open to form fluid handling channels, or the folds may be made tight enough so that little or no space is formed. Other possible arrangements include a "Z" fold, and a pleated absorbent core 6, and other folded shapes, as will be appreciated by those skilled in the art.

The absorbent core 6 preferably is formed using a dry process. Dry processes have numerous benefits over wet processes. For example, in wet processes, the core material is typically immersed in a fluid having a superabsorbent particles mixed or suspended therein, and the core material may require additional drying steps and other steps that add to the complexity and cost of the core forming process. In addition, wet processes often require the absorbent core to be manufactured off of the main assembly line. Dry processes typically have lower operating costs than wet processes because the equipment used in dry processes is typically less complex and can run at higher line speeds. Further, dry forming processes may often be adapted for use directly on the line of conventional diaper machines. A preferred embodiment of the present invention is particularly concerned with using a dry forming process to manufacture absorbent cores having high concentrations of SAP and relatively low basis weights, while overcoming or avoiding the deficiencies of known dry forming processes and machines, as described elsewhere herein.

One challenge with making absorbent cores having high concentrations of SAP and relatively low basis weight fibrous structures, as described above, is to achieve the desired distribution of SAP within the core. In many cases it may be desirable to achieve a uniform distribution of SAP within the core to provide the absorbent garment with uniform absorption capability. In such a case, not only should the SAP be evenly distributed along the length and width of the absorbent core, but it also should be properly distributed throughout the thickness of the core to ensure that the SAP is not subject to gel blocking or other inefficiencies during use. It also is desirable to provide a controlled amount of SAP to the core to prevent overuse of the SAP, which typically is relatively expensive. It may be further desirable to precisely control the distribution of SAP to provide local regions of the core that have greater SAP concentrations than others to provide zoned absorbency. Such concentrations may be along one or more of the absorbent core's length, width and thickness.

Figure 3:
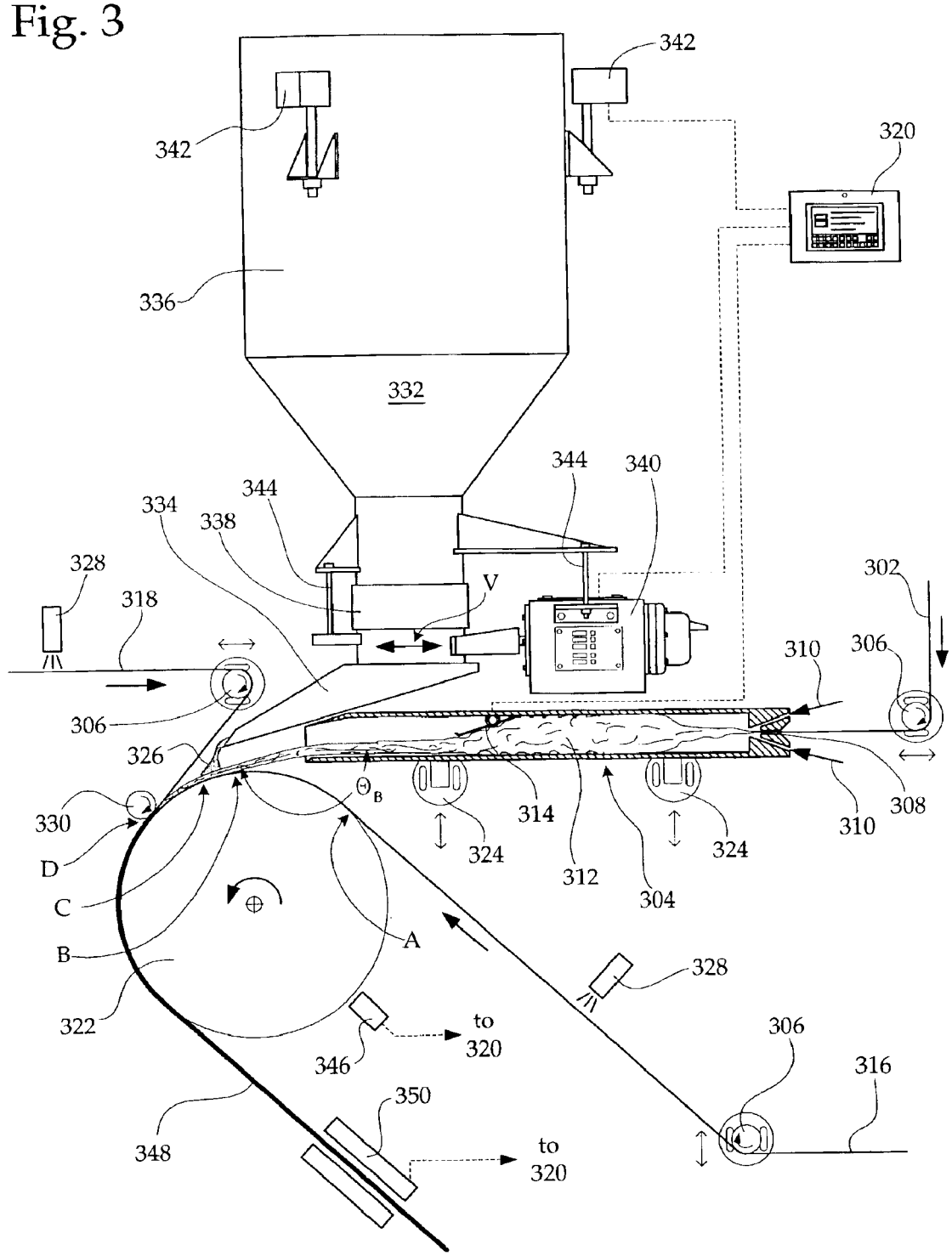
FIG. 3 is a partially cut away side view of a system for dry forming absorbent cores and other structures and machinery according to a preferred embodiment of the present invention, shown in operation and in relation to a portion of an absorbent garment manufacturing line.

Referring now to FIG. 3, a preferred embodiment of an apparatus and method for dry forming composite cores is shown. In the preferred embodiment, a tow supply 302, which may be unopened or partially opened, is provided along a first path to enter a forming jet assembly 304. The supply of tow may comprise any material that is desired to be used as the fibrous structure of the garment's absorbent core 6 and is suitable for use in the process described herein, such as those that have been described elsewhere herein. Those skilled in the art will appreciate that if fibers, fluff, or pulp other than tow fibers are used, forming jet assembly 304 would be replaced by a suitable fiber or fluff forming apparatus, as are well known in the art. A preferred material for the tow supply 302 is a supply of cellulose acetate having a basis weight of about 50 $g/m^2$ to about 100 $g/m^2$, and more preferably of about 76 $g/m^2$. The tension, speed and path of the tow supply 302 may be adjusted by one or more movable pulleys 306, guides (not shown) and/or festoons (not shown), as are known in the art.

The tow supply 302 enters the forming jet assembly 304 and is opened in preparation for being incorporated into absorbent cores. The forming jet assembly 304 comprises a tow inlet 308 at one end into which the tow supply 302 is fed. One or more high velocity jets 310 of air or other gas are projected into the forming jet assembly to impinge upon the tow supply 302 to thereby separate the fibers and "bloom" or open the tow. Preferably, two jets 310 are used and each jet 310 is located proximal to the tow inlet 308 and on opposite sides of the tow supply 302. Each of the jets 310 preferably comprises a flow of air moving at about 17.5 cubic feet per minute through a slit-shaped port that has a length of about 3.94 inches and a width of about 0.003 inches. Similar devices for opening tow are known in the art, and disclosed, for example, in U.S. Pat. No. 5,331,976 to St. Pierre, which is incorporated herein by reference in its entirety and in a manner consistent with the present invention. Other devices and procedures for opening the tow supply 302 may also be used with the present invention, as will be understood by those skilled in the art.

The opened or "bloomed" tow 312 accumulates within the forming jet assembly 304 as it is being used, and the amount of opened tow 312 being consumed may be measured by a level meter 314 (also known as a "dancer"). The level meter 314 may be any suitable electromechanical, optical, or other type of device capable of measuring the amount of opened tow 312 being consumed. In a preferred embodiment, the level meter 314 is a plate that is pivotally attached to a rotary position sensor (such as a commonly known variable resistance or potential device). As the level of opened tow 312 increases or decreases, the plate pivots up and down, thereby changing the output of the rotary position sensor. In a preferred embodiment, the level meter 314 is used as part of a closed-loop feedback algorithm or an open-loop algorithm to meter the rate at which the tow supply 302 is fed into the forming jet assembly 304, and may be integrated into a control system 320.

The control system 320 may comprise any electrical control apparatus that may be configured to control one or more variables based on the measurement of one or more inputs. Although the control system 320 is referred to herein in the singular, it should be understood that a number of independent control systems 320 may be used for various parts of the machinery, and these various systems are referred to collectively herein as a single control system 320. The control system 320 may control any number of variables and have any number of inputs, and may use an open-loop or closed-loop algorithm. Exemplary control systems 320 include programmable logic control (PLC) devices having easily used human machine interfaces, as are known in the art. Of course, the control system 320 may simply comprise a human operator that monitors the various inputs and adjusts the various system variables.

Figure 8:
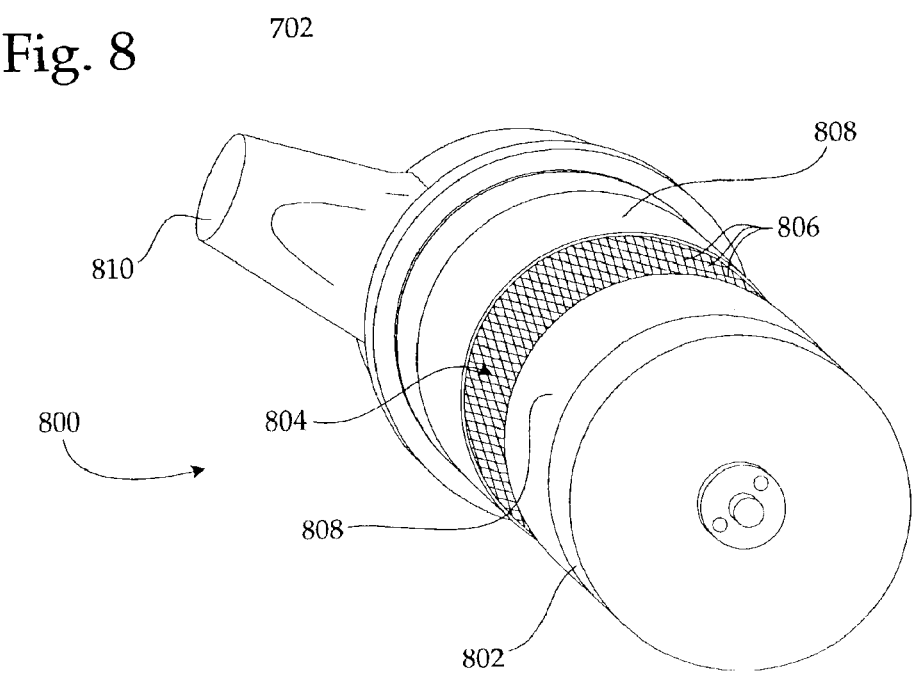
FIG. 8 is an isometric view of a combining drum according to a preferred embodiment of the present invention.

The opened tow 312 preferably is pulled out of the forming jet assembly 304 by a vacuum draw roll 322, such as the combining drum 800 described elsewhere herein in conjunction with FIG. 8, or a similar drawing device. The opened tow 312 exits the forming jet assembly 304 at a tow break angle $\Theta_B$, which may be adjusted by altering the position of the vacuum draw roll 322 (or similar device), or, more preferably, by adjusting the height and angle of the forming jet assembly 304 using adjustable mounts 324. Increasing the tow break angle $\Theta_B$ increases the drag on the opened tow 312 and thereby increases the amount of stretch that the vacuum draw roll 322 imparts on the opened tow 312. Greater stretch reduces the basis weight of the opened tow 312 that is pulled onto the vacuum draw roll 322. The tow forming jet 304 preferably is aligned so that its outlet is tangential to the vacuum draw roll 322 or slightly above a tangent to the vacuum draw roll 322. In a preferred embodiment, the outlet of the tow forming jet 304 is located at a tangent to the vacuum draw roll 322 to about 1 inch above a tangent to the vacuum draw roll 322. In a more preferred embodiment the outlet of the tow forming jet 304 is less than about 0.75 inches above a tangent to the vacuum draw roll 322, and in a most preferred embodiment, the outlet of the tow forming jet 304 is located less than about 0.5 inches above a tangent to the vacuum draw roll 322. In another embodiment, the amount of stretch on the opened tow 312 may instead (or additionally) be regulated by operating the dancer 314 as a baffle (instead of using it as a level meter 314) to pinch down on the opened tow 312 as it is pulled onto the vacuum draw roll 322, and thereby increase the stretch of the opened tow 312. By using the dancer as a baffle, it is expected that adjustments of up to +/−10% may be made to the tow stretch or basis weight.

The tow forming jet's adjustable mounts 324 may be fixed in a desired position during machine operation, or may be actively operated by a control system 320 during operation in response to measurements of the core basis weight or other feedback gathered during operation. Mechanical, electromechanical, pneumatic, hydraulic, or other suitable adjusting devices may be used to actuate the adjustable mounts 324, such as stepper motors, solenoids and hydraulic or pneumatic pistons or rams, and the like. Alternatively, or in addition, the basis weight of the opened tow 312 may be adjusted by increasing or decreasing the speed of the vacuum draw roll 322, with faster speeds generally resulting in a lower basis weight of the opened tow 312.

After the opened tow 312 exits the forming jet assembly 304, a supply of superabsorbent particles 326 is delivered to the opened tow 312, and the tow/SAP composite is encased between first and second casing sheet supplies 316, 318. Alternatively, the tow/SAP composite may be encased within a fold in a single casing sheet. Preferably, as shown in FIG. 3, the opened tow 312 is laid onto a first casing sheet supply 316 before the SAP 326 is fed to the opened tow 312 to help contain the SAP 326 and control the SAP distribution, then the second casing sheet supply 318 is laid on the tow/SAP composite to form an absorbent core subassembly that may be processed into absorbent garments.

The first and second casing sheet supplies 316, 318 encase the opened tow and SAP composite. The first and second casing sheet supplies 316, 318 preferably form the first and second tissue layers 16, 18 of the completed garment, but may also form the topsheet 2 and backsheet 4 of the absorbent garment 10, or any other layers. The first and second casing sheet supplies 316, 318 are preferably wider than the opened tow 312 that forms the absorbent core 6, and their side portions are preferably sealed to one another by bonding or crimping to prevent release of opened tow 312 and particles of SAP. The absorbent core composite 348, comprising the assembly of the first and second casing sheet supplies 316, 318 and the opened tow 312 and SAP 326 core, may be further processed as it is conveyed through the assembly line for inclusion into absorbent garments 10. For example, in a preferred embodiment, the absorbent core composite 348 is severed into individual absorbent cores 6, and the severed ends may be crimped or bonded to prevent the SAP 326 from exiting the ends.

In all cases, at least one of the first and second casing sheets 316, 318 should be liquid permeable and positioned in the garment to face the wearer's body to allow the flow of fluids into the core 6. The other casing sheet supply may optionally be liquid impermeable. The liquid impermeability or permeability of either of the casing sheet supplies 316, 318 may be provided by chemical or physical treatment, or by the proper selection of materials, as is known in the art. In an alternative preferred embodiment, the first and second casing sheets 316, 318 may both be formed from a single sheet of material that is folded to encase the opened tow 312 and SAP 326. In such an embodiment, the structure of various parts of the system may be optionally be modified to facilitate the manufacture of an absorbent core composite having a single casing sheet, as explained in more detail subsequently herein.

It may be desirable to apply an adhesive to one or both of the first and second casing sheet supplies 316, 318 prior to joining them with the opened tow 312 or tow/SAP combination. For example, in one preferred embodiment, an adhesive is applied to the entire width of one or both of the casing sheet supplies 316, 318 by adhesive applicators 328 before they are joined with the opened tow 312 to provide a better bond between the casing sheets 316, 318 and the tow/SAP composite. In such an embodiment, the adhesive may also function to fix a portion of the SAP particles 326 in place. In another preferred embodiment, the supplies of casing sheet material 316, 318 are wider than the tow/SAP composite, and adhesive is applied along the lateral edges of one or both of the casing sheet supplies to join them to one another, thereby sealing in the tow/SAP composite. Other uses of adhesives will be apparent to those skilled in the art based on the teachings provided herein.

A preferred adhesive for these and other embodiments is H2561U hot melt construction adhesive, available from Ato Findley, Inc. of Wauwatosa, Wis. Other suitable adhesives, known in the art, may be used provided they do not excessively impair the desired properties of the casing sheet material (as described elsewhere herein), or add excessive stiffness to the absorbent core 6. For example, other adhesives may include HL-1258 by H. B. Fuller Company of St. Paul, Minn.; Findley 2031 and H2587-01 by Ato Findley Inc. of Wauwatosa, Wis.; and NS34-5665 by National Starch Co. of Bridgewater, N.J. Other adhesives that may be used include 34-578A by National Starch Co. of Bridgewater, N.J. In another preferred embodiment, the adhesive may be selected to impart desired properties to the casing sheet supplies 316, 318. For example, an adhesive may be used to render one of the casing sheet supplies 316, 318 fluid impervious, opaque, hydrophobic (or hydrophilic), and so on the adhesive may also be water soluble or have other beneficial properties. Adhesive applicators that may be used with the present invention include spray applicators, such as those provided by Nordson Corporation of Westlake, Ohio, or other suitable applicators, as are known in the art.

Still referring to FIG. 3, in a preferred embodiment the absorbent core composite 348 is assembled in four procedures that take place as the various parts of the assembly are pulled onto the rotating vacuum draw roll 322. In the first step, which takes place at location A, the first casing sheet supply 316 is drawn onto the vacuum draw roll 322. In the second step, at location B, the opened tow 312 is drawn onto the vacuum draw roll 322 to overlay the first casing sheet supply 316 after being pulled out of the forming jet assembly 304. In the third step, at location C, a supply of SAP 326 is deposited onto the opened tow 312 by the vibratory feeder 332, as described herein. And in the fourth step, at location D, the second casing sheet supply 318 is brought in to overlie the first casing sheet supply 316, opened tow 312 and deposited SAP. Those skilled in the art will appreciate that these steps may be performed using equipment other than that specifically described herein, and may also be performed in various different orders, with some of the steps being rearranged, omitted or combined, or with additional steps being performed. Such variations are generally within the scope of the present invention.

Also in a preferred embodiment, a lay on roll 330 is used to press the second casing sheet supply 318 against the tow/SAP composite and the first casing sheet supply 316. The lay on roll 330 helps flatten the core assembly and improves the edge seals between the first and second casing sheet supplies 316, 318. The lay on roll 330 may also be equipped to provide ultrasonic, heat, or other bonds between one or more of the first and second casing sheets 316,318 and the tow/SAP composite. In such an embodiment, the lay on roll 330 may cooperate with the vacuum draw roll 322 or other device to create the desired bonds. For example, portions of the lay on roll 330 may form ultrasonic horns, while corresponding portions of the vacuum draw roll 322 form ultrasonic anvils that, together, form an ultrasonic bond between the first and second casing sheet supplies 316, 318.

The superabsorbent particles preferably are provided by a vibratory feeder 332, however any other suitable SAP feed device, such as auger-type feeders and SAP sprays also may be used. The vibratory feeder 332 comprises a feed tray 334 that is attached to and driven by a motor 340. The motor 340 vibrates the feed tray 334, moving it back and forth in the direction of vibration V, as indicated by the double-headed arrow in FIG. 3. The feed tray 334 is supplied from above by a hopper 336 by way of a flexible coupling 338 that helps isolate the hopper 336 from the movement of the feed tray 334. The vibratory feeder is preferably suspended on one or more, and most preferably three, scales 342 that weigh the vibratory feeder 332 and its contents. The vibratory feeder 332 is preferably positioned so that none of its moving parts, particularly the motor 340 and feed tray 334 strike other parts of the machinery during operation.

The hopper 336 is preferably selected to provide consistent flow characteristics for a variety of superabsorbent polymers or other particulate and fibrous additives. In particular, it is preferred that the hopper 336 should flow all of its contents in a regular manner, described as "mass flow," so that few or none of the particles become stuck in the hopper 336, and do not experience sudden surges in the flow rate. Mass flow is present when essentially all of the material in the hopper is in motion whenever any material is withdrawn. This type of flow pattern is also described as first-in-first-out flow. In order to provide the desired mass flow, the hopper 336 is preferably designed to avoid "bridging" (i.e., when particles become lodged in the hopper by forming a "bridge" or arch-like structure that resists flowing), and to avoid "ratholing" (i.e., when a column of particles flows through the center of the hopper 336, but those particles along the walls do not flow). When the hopper 336 provides mass flow, it is not necessary to provide undesirable external forces, which may damage or redistribute the particles, to shake unmoving particles free. Mass flow may be obtained by providing the hopper 336 with relatively smooth interior walls and by avoiding the use of shallow flow angles within the hopper 336. The design may vary depending on the particulate matter or SAP 326 being held in the hopper 336, and it may be desirable to test the properties of the material, such as the material's slip angle and angle of repose, to obtain a suitable hopper design. The design of mass flow hoppers is generally known in the art, and a skilled artisan will be able to design a suitable hopper without undue experimentation based on the teachings provided herein.

In one embodiment, the hopper has a capacity of about 1.5 $ft^3$ to about 10 $ft^3$, and more preferably about 2.25 $ft^3$ to about 6 $ft^3$, and most preferably about 3 $ft^3$. Also in a preferred embodiment, the hopper 336 discharges through an outlet having a diameter of about 4 inches to about 12 inches, and more preferably about 5 to about 9 inches, and most preferably about 7 inches. The hopper 336 may be supplied and refilled with SAP using any device and method known in the art. In a preferred embodiment, the hopper 336 is filled by a screw (or "auger") type conveyor that moves SAP from a supply source into the hopper 336. The design of such hoppers 336, conveyors and supply sources is known in the art, and a skilled artisan will be able to provide a hopper 336 for use with the present invention without undue experimentation based on the teachings provided herein.

In a preferred embodiment, the hopper 336 is derived from a SOLIDSFLOW MODEL 5007 DRY MATERIAL FEEDER. Also in a preferred embodiment, the hopper 336 is supplied and refilled from a SOLIDSFLOW MODEL SBS BULK BAG DISCHARGE STATION using a FLEXICON flexible screw (auger) conveyor, which is controlled by a SOLIDSFLOW MODEL 1200 LOSS-IN-WEIGHT CONTROLLER. All of these devices are available from SolidsFlow Corporation of Fort Mill, S.C.

The vibratory feeder 332 may be suspended from one or more, and most preferably three, scales 342 that measure the weight of the vibratory feeder 332 and its contents. The scales may be used to calculate the amount of SAP 326 that is being distributed onto the opened tow 312. Such systems are commonly known as "loss-in-weight" systems, as they continuously measure the reduction in weight of the vibratory feeder 332 as its contents are being emptied. The conveyors and supply sources that feed into the hopper 336 may also be suspended on scales so that SAP may be added to the hopper during operation, while still being able to calculate the amount of SAP being deposited onto the opened tow 312. In a preferred embodiment, the loss-in-weight measurements of the scales 342 are used with a closed-loop feedback circuit to control the amount of SAP 326 that is deposited onto the opened tow 312. Such a circuit is preferably integrated into a control system 320 that may control other features and operation of the vibratory feeder 332 and related devices. The scales 342 may also be used to determine when it is necessary or desirable to refill the hopper.

The scales 342 are preferably able to read to an accuracy that allows useful determination of the amount of SAP being deposited onto the opened tow 312. In a preferred embodiment, the scales 342 read to an accuracy of about +/−10 grams, and more preferably of about +/−1 gram, and most preferably of about +/−0.1 gram. In a preferred embodiment, the scales 342 comprise strain gauge-type load measurement cells, such as those available under the designation SOLIDSFLOW MODEL 1000 SCALE ASSEMBLY from SolidsFlow Corporation of Fort Mill, S.C. The design, construction, and use of scales suitable for use with the present invention is known in the art.

A flexible coupling 338 preferably joins the hopper 336 to the feed tray 334. The flexible coupling 338 is used pass SAP or other additives from the hopper 336 to the feed tray 334, while simultaneously isolating the hopper 336 from the vibratory movement of the feed tray 334 and motor 340. The flexible coupling 338 may comprise any durable flexible material, such as canvas and other cloths, or natural or synthetic rubbers. It is preferred that the flexible coupling does not damp or impede the desired vibrating motion of the feed tray 334 and motor 340, and thereby impair the ideal SAP feeding. For example, if the flexible coupling 338 is too rigid, it will reduce the ability of the motor 340 to vibrate the feed tray 334 because it will resist deformation, effectively increasing the mass of the feed tray 334. Also, if the flexible coupling 338 is too elastically resilient, it will tend to store energy created in it when the feed tray 334 and motor 340 are vibrating, and return this stored energy in an uncontrolled manner (i.e., vibrate on its own) thereby creating additional uncontrolled vibrations in the feed tray 334 and motor 340. It also is preferred that the flexible coupling 338 be as light as possible so as to reduce the inertia that must be overcome by the motor 340 during operation. In a preferred embodiment, the flexible coupling 338 comprises a rubber material having a diameter and shape selected to join the outlet of the hopper 336 with the inlet chute 402 of the feed tray 334.

The feed tray 334 and motor 340 preferably are suspended below the hopper 336 by flexible mounts 344 that allow the motor 340 and feed tray 334 to move relative to the hopper 336. The flexible mounts 344 may comprise rods having flexible or pivoting couplings joining them, at each end, to the hopper 336, motor 340 and feed tray 334. In a preferred embodiment, the flexible mounts 344 are designed to convey a minimal amount of vertical movement or vibration to the hopper 336, which may cause the scales 342 to read inaccurately. In such a preferred embodiment, the flexible mounts 344 may be joined to one or more of the hopper 336, motor 340 and feed tray 334 by a dry or liquid-filled elastomeric bushing or coupling. The design and selection of such vibration- and movement-damping couplings are known in the art, and a skilled artisan will be able to select or produce an appropriate coupling system based on the teachings provided herein.

Figure 4:
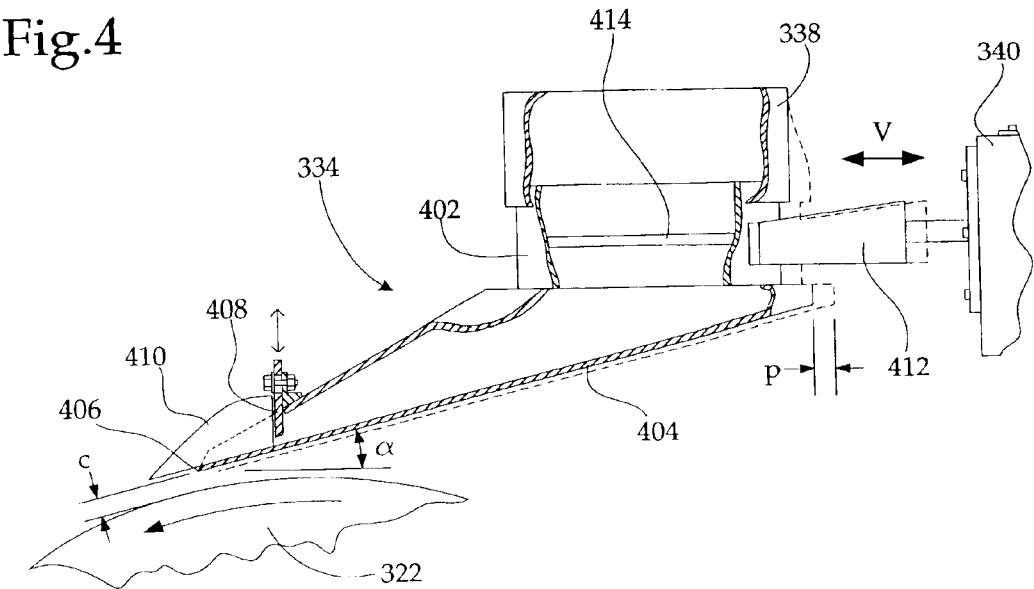
FIG. 4 is a partially cut away view of a feed tray according to a preferred embodiment of the present invention, shown at one end of its range of movement and showing the other end of its range of movement in dashed lines.

Referring now to FIG. 4, the feed tray 434 preferably comprises an inlet chute 402 that is attached to the flexible coupling 338 to receive SAP 326 from the hopper 336. A pan 404 extends away from the inlet chute 402 at a downward angle a to an outlet edge 406 of the feed tray 334. The pan 404 may also comprise multiple sections that descend at varying angles. The feed tray 334 preferably is covered along most of its length to prevent disturbances of the SAP 326 or other particulate additives. The covered portion preferably terminates at an adjustable gate 408 located near the outlet edge 406 of the feed tray 334. The adjustable gate 408 is spaced above the pan 404 and generally divides the feed tray into an upstream portion from which the SAP 326 flows and a downstream portion. The adjustable gate 408 may be operated manually, or may be opened and closed by an actuating device, such as an electromechanical, mechanical, pneumatic, or hydraulic device. Such an actuating device may optionally be controlled by a control system 320 using a closed-loop feedback algorithm or open-loop algorithm. Such actuating devices are known in the art, and a skilled artisan will be able to employ a suitable actuating device without undue experimentation. Of course, in one embodiment the gate may be a fixed gate, rather than an adjustable gate.

Figure 7:
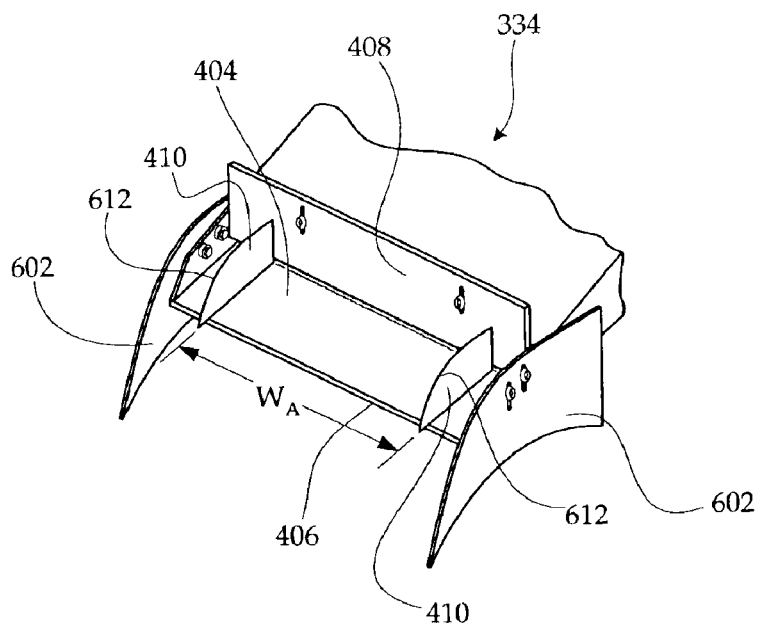
FIG. 7 is an isometric view of the outlet portion of a feed tray according to a preferred embodiment of the present invention.

In a preferred embodiment, the SAP 326 or other particulate additive material exits the feed tray 334 at its outlet edge 406 in a curtain-like stream having a consistent flow rate across its entire width. Referring to FIG. 7, the active width $W_A$ of the feed tray 334 is the width of the portion of the feed tray 334 from which the SAP 326 flows (which may be affected by the use of SAP guides 410, as described elsewhere herein), and generally corresponds to the width of the SAP flow. The active width $W_A$ may vary from one application to the next, and may be varied during operation by using, for example actuated pivoting SAP guides 410 that move together and apart under the control of a control system 320. Generally, the active width $W_A$ preferably is approximately the same width as the opened tow 312. In one embodiment the active width $W_A$ is about 2 inches to about 12 inches, and is more preferably about 3 inches to about 10 inches, and, in a particularly preferred embodiment, the active width $W_A$ is as about 3.75 inches to about 4 inches.

Figure 15:
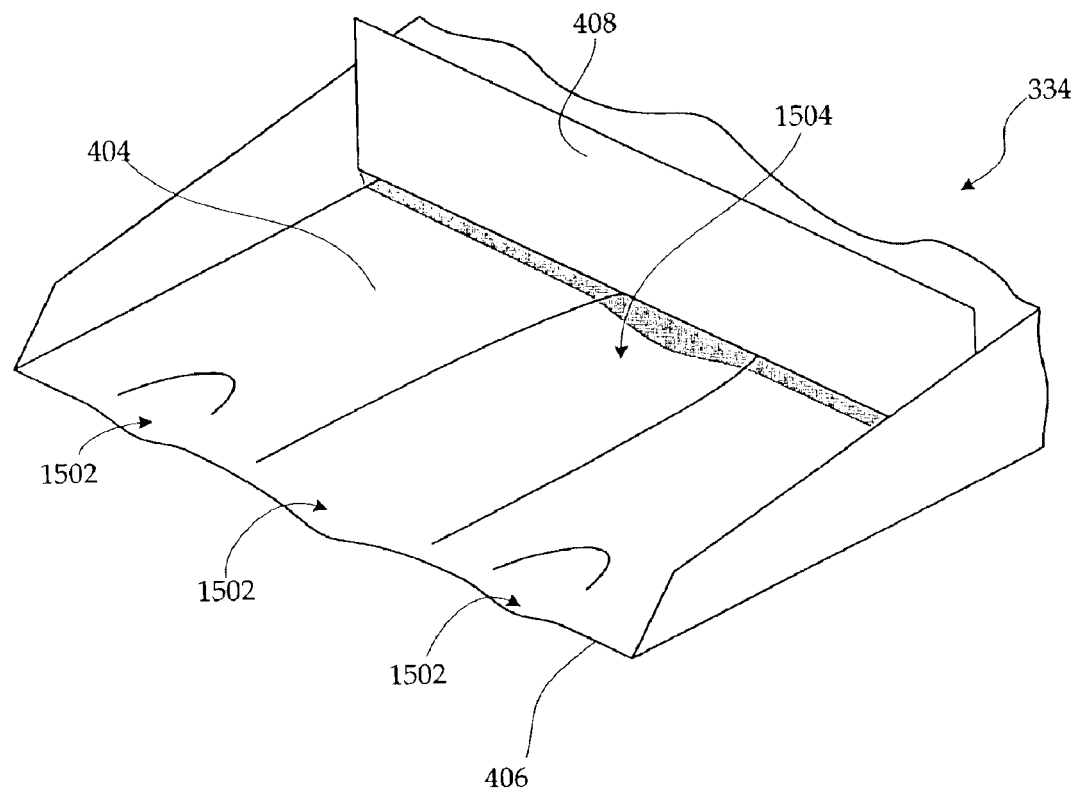
FIG. 15 is an isometric view of the outlet portion of a feed tray according to another embodiment of the present invention.

In other embodiments it may be desirable to vary the flow rate of the SAP 326 in particular areas to provide zoned absorbency. Referring now to FIG. 15 the pan 404 may be contoured or shaped to provide concentrated flows of SAP during operation or to otherwise control the flow of the SAP. For example, in one embodiment the pan 404 may have one or more depressions 1502 along the outlet edge 406 that effectively increase the downward angle a at the depressions 1502. In such an embodiment, the SAP 326 may tend to funnel into the depressions 1502, and those portions of the opened tow 312 that pass beneath the depressions 1502 should receive a relatively high concentration of SAP 326. In another embodiment, the pan 404 may have troughs 1504 that extend below the adjustable gate 408, effectively increasing the height h of the adjustable gate 408 at those points to increase the flow rate of SAP through the troughs 1504. Such troughs 1504 may extend to the outlet edge 406 to additionally act as depressions 1502, as described above. Other variations in the outlet edge 406 and pan 404 geometry will be apparent to those skilled in the art based on the teachings provided herein.

In one embodiment, the feed tray 434 may have more than one inlet chute 402 so that a number of different supplies of SAP may be fed into it. The supplies of SAP may comprise different types of SAP that are blended or isolated from one another using internal baffles and guides. In such an embodiment, for example, one type of SAP may be distributed to the lateral sides of the opened tow 312, and another type of SAP may be distributed to the central region of the opened tow 312. Other variations and uses of a feed tray 334 having multiple inlet chutes 402 will be apparent to those skilled in the art based on the teachings provided herein.

SAP guides 410, comprising vertical or angled strips of material, optionally may be integrated into the feed tray 334 on either side of the adjustable gate 408 to serve a number of purposes. The SAP guides are preferably attached to the pan 404, but may also be attached elsewhere to the feed tray 334 or to other objects. In a preferred embodiment, the guides contain the lateral movement of the SAP 326 so that it falls only in a center region of the opened tow 312. In another preferred embodiment, the SAP guides 410 isolate the flow of SAP 326 from turbulent airflow around the feed tray 334 to provide more even SAP distribution. The SAP guides 410 may be proximal to the outlet edge 406, as shown in FIG. 4, or may be located elsewhere on the pan 404. The SAP guides 410 may also be used to isolate or blend different supplies of SAP. In one embodiment, the SAP guides 410 may also comprise additional vertically stacked layers, in addition to the pan 404, that may contain separate flows of SAP. In a preferred embodiment, the SAP guides 410 are spaced apart by about 3.75 inches to about 4 inches to provide about a 3.75 inch to about 4 inch wide flow of SAP.

Figure 5A:
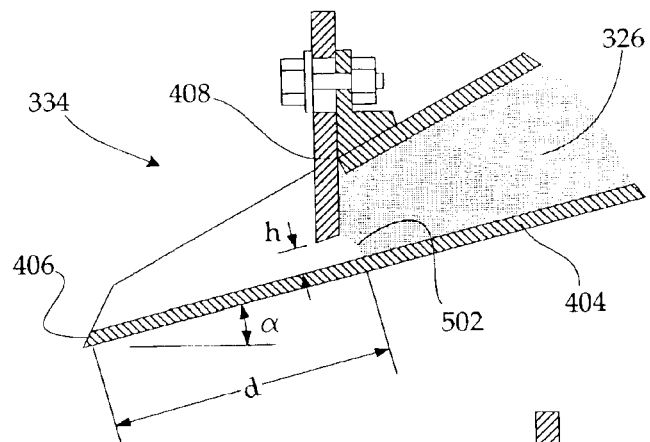
FIG. 5A is a cut away view of a portion of a feed tray according to a preferred embodiment of the present invention.
Figure 5B:
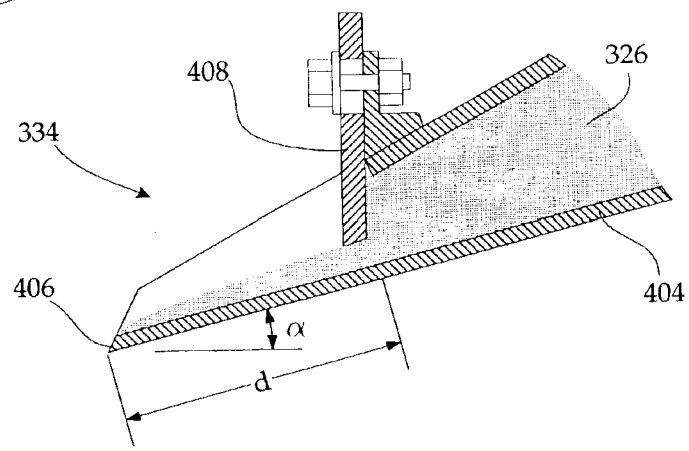
FIG. 5B is a cut away view of a portion of another feed tray according to a preferred embodiment of the present invention.

Referring now to FIGS. 5A and 5B, the feed tray 334 operates on the principle that particulate solids within them, such as SAP 326, will rest at their angle of repose until disturbed by vibrations induced by the motor 340. This principle of operation is more fully disclosed in U.S. Pat. No. 3,973,703 to Peschl, which is incorporated by reference herein in its entirety and in a manner consistent with the present invention (hereafter referred to herein as "Peschl"). It should be understood that, although the inventors provide various theories on the modes of operation of the vibratory feeder 332, the invention is not intended to be limited to these or other modes or theories of operation.

It has been found that the flow of the SAP 326 generally may be influenced by the properties of the SAP, the downward angle a of the pan 404, the rate of vibration of the motor 340, the trailing distance d of the pan 404, and the height of the adjustable gate 408. In the embodiment shown in FIG. 5A, the feed tray 334 is shown at rest, with the SAP 326 being contained within the feed tray 334. In the embodiment of FIG. 5A, the downward angle a is greater than the angle of repose of the SAP 326, and so any SAP remaining along the trailing distance d of the pan 404 slides off the pan 404 after the motor 340 stops vibrating. The remaining SAP 326 is caught behind a bridge 502 of SAP that forms by friction between the particles of SAP, cohesion between the SAP particles, or both. The adjustable gate height h may be adjusted to provide ideal SAP containment and control. Raising the adjustable gate 408 generally provides a greater SAP flow rate for a given motor vibration frequency, while lowering the adjustable gate 408 generally provides the opposite result. The adjustable gate height h preferably is adjusted to ensure that a bridge 502 forms promptly after the motor 340 stops vibrating the feed tray 334 to stop the flow of SAP 326 as quickly as possible.

The flow rate of the SAP generally follows the vibration rate of the motor 340, and stops flowing almost immediately upon shut down of the motor 340. Generally, faster motor vibration rates provide greater SAP flow rates and slower motor vibration rates provide a slower SAP flow rate. There is little or no appreciable time delay between changes in the motor frequency and the flow rate of the SAP 326, so the vibratory feeder 332 provides relatively accurate control of the SAP flow, especially when compared to known methods of distributing SAP onto opened tow 312 or fluff pulp.

It should be noted that SAP remaining on the trailing distance d of the pan 404 may continue to flow at an uncontrolled rate after the motor frequency changes, but such lag time has not been found to cause an appreciable detriment to the device's ability to accurately deposit SAP 326 onto the opened tow 312. If a detriment is found, however, the trailing distance d may be reduced to make the SAP flow rate follow the motor frequency variations more closely. Reducing the trailing distance may also increase the flow rate of the SAP for a given motor frequency and adjustable gate height h, as is explained in more detail in Peschl. In one embodiment, the trailing distance may be reduced to zero, and the outlet edge 406 even may be within the upstream portion of the feed tray 334 (i.e., the adjustable gate 408 may be located beyond the outlet edge 406).

In a more preferred embodiment, shown in FIG. 5B, the downward angle a may be less than the SAP's angle of repose and slip angle (i.e., the angle at which the SAP 326 will slide down the surface of the pan 404), so that when the feed tray 334 is at rest the SAP remaining along the trailing distance d stays on the pan 404. In such an embodiment, the aforementioned lag between SAP flow and motor frequency changes associated with the SAP located in the trailing distance d may be reduced.

Referring back to FIG. 4, it has been found that the feed tray's outlet edge 406 should be located as close as possible to the vacuum draw roll 322. Reducing the offset distance c between the outlet edge 406 and the vacuum draw roll 322 provides a number of benefits. In particular, minimizing the offset distance c allows the SAP to fall onto the opened tow 312 as quickly as possible, minimizing any redistribution or diffusion of SAP 326 that may be caused during a longer fall by turbulent air flowing around the feed tray 334 and by interaction between the SAP particles 326. Reducing the offset distance c also decreases the lag time between changes in motor speed 340 and changes in the amount of SAP 326 being distributed to the opened tow 312. In a preferred embodiment, the offset distance is about 0.25 inches to about 4.00 inches, and more preferably about 0.375 inches to about 1.00 inch, and most preferably about 0.50 inches.

The minimum value for the offset distance c may be affected by machine operating tolerances, such as to prevent contact between the open tow 312 or the vacuum draw roll 322 and the vibrating feed tray 334, or by other factors, such as the tolerances of the casing sheet supplies 316, 318 and opened tow 312. For example, in a preferred embodiment, the offset distance c is at least about 0.50 inches to allow passage of clumped aggregations of opened tow 312, that may be present during startup and during other operating conditions.

In a preferred embodiment that may be used with a variety of SAPs, the downward angle $\alpha$, as measured relative to horizontal, is about 10 degrees to about 45 degrees, and more preferably about 12 degrees to about 30 degrees, and most preferably about 15 degrees. Also in a preferred embodiment, the adjustable gate height h is about 0.10 inches to about 1.00 inches, and more preferably about 0.125 inches to about 0.75 inches, and most preferably about 0.25 inches to about 0.50 inches. Also in a preferred embodiment, the trailing distance d is about 0.25 inches to about 8 inches, and more preferably about 2 to about 6 inches, and most preferably about 4 inches. Also in a preferred embodiment, the inlet chute 402 has a diameter of about 4 inches to about 12 inches, and more preferably about 5 to about 9 inches, and most preferably about 7 inches. In a preferred embodiment, the feed tray 334 may be derived from a SOLIDSFLOW MODEL 5000 DRY MATERIAL FEEDER, available from SolidsFlow Corporation of Fort Mill, S.C.

Figure 6:
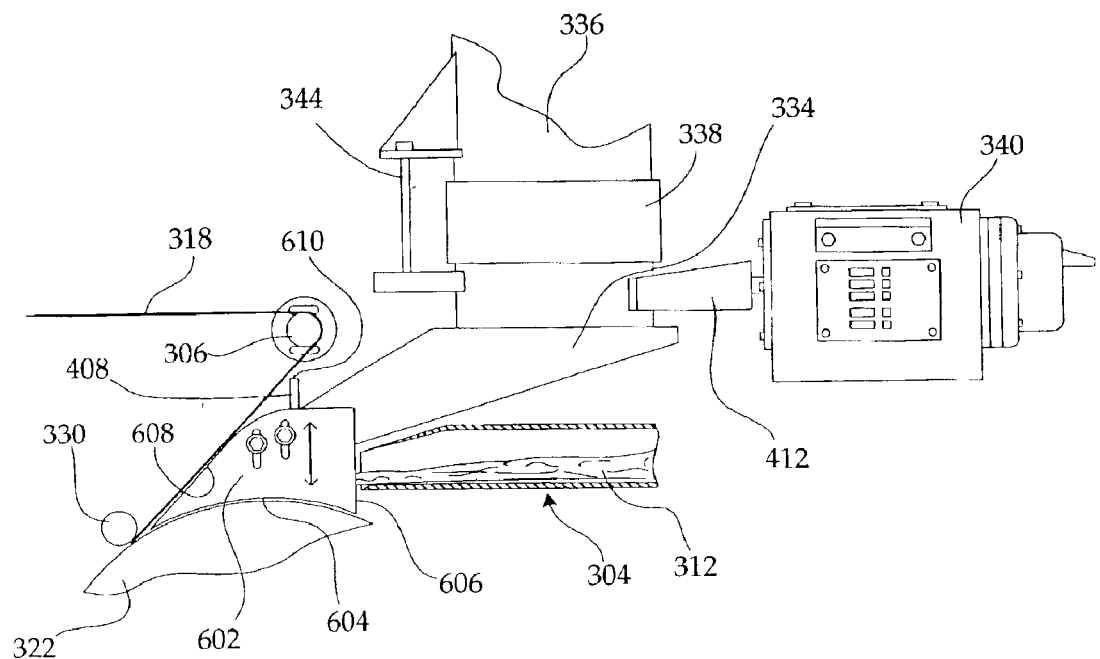
FIG. 6 is a partially cut away side view of a feed tray, motor and side plates according to a preferred embodiment of the present invention.

Referring now to FIGS. 6 and 7, the feed tray 334 preferably is equipped with side plates 602 that help isolate the SAP 326 and opened tow 312 from lateral airflow and may help contain the lateral movement of SAP 326 after it exits the feed tray 334. Such lateral airflow and other airflow may disturb the desired distribution of SAP onto the opened tow 312. The side plates 602 are preferably oriented approximately parallel to the machine direction of the opened tow 312 (i.e., within about 20 degrees of parallel) and sized to substantially reduce or block air from flowing laterally into the area beneath the feed tray 334. Preferably, a first edge 604 of each side plate 602 is located proximal to the vacuum draw roll 322 (or other similar drawing device); and a second edge 606 of each side plate 602 is located proximal to the forming jet assembly 304. The side plates 602 are preferably shaped and sized so that they do not strike any other parts of the machine as they are vibrated back and forth. A third edge 608 of each side plate 602 preferably is adapted to conform to the second casing sheet supply 318 to help prevent lateral airflow from above the feed tray from encroaching upon the supply of SAP 326. In such an embodiment, it also may be desirable for the top edge 610 of the adjustable gate 408 to be proximal to the second casing sheet supply 318 to further reduce the amount of air that flows in to potentially disturb the SAP 326. The SAP guides 410 may also have an edge 612 contoured to be adjacent to the second casing sheet supply 318 to further inhibit the development of undesirable airflow near the SAP 326. The side plates 602 preferably may be adjusted in at least the vertical direction, as indicated by the double-headed arrow in FIG. 6. In other embodiments, the side plate 602 may be attached to something other than the feed tray 334, but in such embodiments, care should be taken to prevent the moving feed tray 334 from striking the side plates 602 during operation.

Referring back to FIG. 4, the motor 340 is used to initiate and modulate the flow of SAP 326 out of the feed tray 334. The motor 340 vibrates the feed tray 334 by moving it back and forth in the direction of vibration V, as indicated by the double-headed arrow in FIG. 4. In a preferred embodiment, both the pitch p and frequency of the motor 340 may be adjusted to modulate the flow of SAP 326. It has been found that increasing the motor's pitch p (i.e., the distance traversed by the motor during each cycle) generally increases the SAP flow rate, and vice-versa. Also, as noted before, it has been found that increasing the motor's frequency generally also increases the SAP flow rate, and vice-versa.

The effectiveness of the motor 340 and amount of control provided by the motor 340 are affected by the weight and rigidity of the feed tray 334. If the feed tray 334 is too heavy, its inertia will resist the forces imparted upon it by the motor 340, and the motor 340 may not be able to accelerate and decelerate it back and forth to create the desired pitch p distance or frequency vibrations. If the feed tray 334 is not rigid enough, it will flex as the motor 340 imparts forces on it. As the feed tray 334 flexes, it absorbs the energy that was intended to move the feed tray 334 and does not accurately follow the path intended by the motor 340. The energy absorbed by a flexible feed tray 334 may be released in the form of undesirable variations in the intended pitch p and frequency of vibration. It has been found that it is generally desirable to make the feed tray 334 as light and as rigid as possible in order to provide the greatest amount of control of the SAP flow.

In a preferred embodiment, the motor 340 is coupled to the feed tray 334 through a coupling 412. In order to provide accurate transmission of the motor's vibrations to the feed tray 334, the coupling 412 should be rigid in the vibration direction V, and the coupling 412 preferably has a box-like shape or C-shape. Also in a preferred embodiment, the inlet chute 402, which may comprise a relatively large open space that may be susceptible to undesirable flexing, is reinforced with a structural member, such as a tubular brace 414 aligned in the vibration direction V. In an embodiment in which the inlet chute has a diameter of about 7 inches it has been found that a tubular brace 414 of about 1 inch diameter is suitable to reduce undesirable flexure in the inlet chute 402 without adversely affecting the flow of SAP through the inlet chute. In other embodiments, in which the inlet chute 402 contains baffles or other internal flow-directing or flow-controlling structures, these structures may also serve to increase the feed tray's rigidity, making it unnecessary to reinforce the inlet chute 402.

As noted before, the motor 340 and feed tray 334 are suspended beneath the hopper 336 by flexible mounts 344 that allow both the motor 340 and the feed tray 334 to move independently of the hopper 336. As such, as the motor 340 vibrates the feed tray 334 back and forth, the motor 340 itself may also move back and forth. In a preferred embodiment, the mass of the motor 340 is significantly greater than the combined mass of the feed tray 334 and the SAP 326 contained therein, and so the movement of the motor 340 will be insignificant relative to the movement of the feed tray 334. In such an embodiment, the motor's pitch p will be almost entirely converted into movement of the feed tray 334 (as is shown in FIG. 4). If, however, the motor 340 does experience a significant amount of movement, more of the pitch p will be converted into the motor's movement, and less of the pitch will result in movement of the feed tray 334. This reduction in the movement of the feed tray 334 may result in less effective SAP distribution and control. If it is found that the movement of the motor negatively affects the SAP distribution and control, the motor's movement may be restricted, or the pitch p may be increased to increase the effective movement of the feed tray 334. Other measures may also be taken to counteract such negative affects. Those skilled in the art will be able to measure or calculate the movement of the motor 340 and feed tray 334 and make accommodations in the design of the apparatus for such movements using the teachings provided herein.

In a preferred embodiment, the motor 340 comprises an electromagnetic vibrator, such as those supplied by Eriez, Corporation of Erie, Pa. as Model Number 30A, part number 3N-56743. Such a motor may be selected to be driven by any available power source, such as a 115 volt, 60 Hz power source. The motor may also require specific support or drive hardware and software, such as an Eriez VTF signal following controller board that is supported by and AB SLC 0–20 mA analog card, available from Allen-Bradley Company of Milwaukee, Wis. Other motors 340 may also be used, such a rotary motor that is configured to provide cyclical lateral movement or vibrations to the feed tray 334. Other useful motors 340 include pneumatic, magnetic, electric and hydraulic actuators, and the like, as long as they can provide the necessary forces to vibrate the feed tray 334 at the desired pitch p and frequency. Electromagnetic vibrators are preferred, as they typically provide relatively controllable movement and consume less energy than other devices.

In one embodiment that should be suitable for dispensing a variety of SAP materials, the motor 340 may be operated from a standstill (zero Hz) up to about 430 Hz, and more preferably up to about 520 Hz, and most preferably up to about 600 Hz. In a preferred embodiment that should be suitable for dispensing a variety of SAP materials, the frequency is approximately constant, and the flow rate of the particulate matter is controlled by modulating the motor's pitch. In such a preferred embodiment, the motor frequency is about 60 Hz, and the pitch p of the motor variable between about 0.01 inches to about 0.125 inches, and more preferably about 0.02 inches to about 0.10 inches, and most preferably about 0.04 inches to about 0.08 inches. Such adjustments may be obtained, for example, by varying the voltage of the motor between about 0 and about 90 volts.

Such a vibratory feeder 332 may be adapted to provide a high volume of SAP flow, and may be used at relatively high manufacturing line speeds. It is anticipated that a vibratory feeder produced according to a preferred embodiment of the present invention may be used with an assembly line producing diapers at a rate in excess of 600 products per minute. The vibratory feeder 332 preferably can feed superabsorbent polymer or other additives at a rate of about 10,000 grams per minute (g/min) to about 20,000 g/min, and more preferably at a rate of about 12,500 g/min to about 17,500 g/min, and most preferably at a rate of about 15,000 g/min. In a preferred embodiment, the hopper 336 is fed by a screw-type conveyor or other conveyor that has a capacity to maintain a useful level of SAP 326 in the vibratory feeder 332. The conveyor may have a feed rate that is less than the maximum feed rate of the vibratory feeder 332, so long as the average feed rate of the vibratory feeder 332 does not exceed the average feed rate of the conveyor.

Superabsorbent polymers and other particulate additives can be relatively expensive, and so it is often desirable to minimize the amount of SAP that is placed in the core and to "zone" such additives only where they are most beneficial for the final product. Such zoning is also particularly beneficial in tow-based absorbent cores because the lack of fluff pulp in such cores may reduce the overall wicking capability of the core, making it more important to place the SAP closer to the location where fluid is likely to strike the garment. In a preferred embodiment, the motor 340 is controlled by a control system 320 to provide a desirable distribution of SAP 326 into the opened tow 312. In one preferred embodiment, such a control system 320 may be used to operate the motor 320 to deposit a steady stream of SAP 326 onto the opened tow 312 to provide a uniform opened tow/SAP mixture in the absorbent cores that are ultimately formed by the process. In another preferred embodiment, the control system may cyclically increase and decrease the pitch p and/or frequency of the motor 340 to deposit a pulsating supply of SAP 326 to the opened tow 312, thereby providing the absorbent cores with targeted concentrations of SAP that provide the garment 10 with zoned absorbency. Preferably, the control system 320 uses a closed-loop feedback method that considers various factors in determining how much SAP to distribute at any given moment.

In a preferred embodiment, the control system 320 is provided with information about how fast the assembly line is running by using, for example, a tachometer 346 on the vacuum draw roll 322 or by any other suitable line speed measuring device (See FIG. 3). By integrating such a line speed measuring device into the control system 320, the control system 320 may be programmed to increase or decrease the pitch p or frequency of the motor 340 to vary the SAP flow rate as the product manufacturing rate changes, thereby providing all of the products with the proper amount of SAP, regardless of the assembly line speed. Such a capability provides a lower rate of product rejection during transitional phases, thereby improving the overall efficiency of the manufacturing process.

In another preferred embodiment, the output of the scales 342 is integrated into the control system 320. By considering the weight of the SAP being distributed, as measured by the scales 342, the control system 320 may programmed to modulate the motor 340 to accurately distribute SAP at the desired flow rate. In such an embodiment, the control system 320 may also accommodate for deviations in the flow characteristics of the SAP particles to continue to provide an even flow, such as by increasing the vibration rate if it is found that the SAP is not flowing as rapidly as expected, and vice-versa. Such deviations may be caused by typical variations in the shape, size, humidity, density, or other features of the SAP, or may be caused when a different SAP product is used in a machine that was originally set up for another type of SAP or set up for a SAP provided by a different supplier.

A closed-loop feedback control system 320 may also be programmed to stop distributing SAP in the event that a fault is detected in the processing line. For example, if a fault detection circuit tied into the control system 320 determines that one or more products will be defective upon completion, the flow of SAP may be stopped so that the defective products will not receive SAP. In such an embodiment, it may be desirable to produce the absorbent cores of the garments as late as possible in the manufacturing process in order to detect as many defects as possible before preparing the absorbent core 6 for each product.

In one embodiment, a SAP concentration detection device 350 (FIG. 3) may be integrated into the control system 320 to provide further detection and control capabilities to the control system 320. The concentration detection device 350 may be located to measure the amount and/or location of SAP in the assembled absorbent core composite 348. If the amount of location of the SAP is not present as desired, the concentration detection device 350 may signal this to the control system 320 so that appropriate corrections in the SAP feed rate may be made. Those skilled in the art are capable of designing or utilizing a suitable SAP concentration detection device 350 using the guidelines provided herein.

The flow rate of the SAP may also be controlled by a control device 320 by actively adjusting the height h of the adjustable gate 408 during operation. As noted before, the adjustable gate 408 may be raised and lowered during operation to increase and decrease, respectively, the flow rate of the SAP 326. Such adjustments may also be made to provide a cyclically fluctuating amount of SAP to the opened tow 312 to create targeted regions of relatively high SAP concentration for zoned absorbency. In such an embodiment, the control device 320 may operate the adjustable gate 408 in conjunction with the scales 342, tachometer 346, concentration detection device 350, or other sensors to provide closed-loop feedback control of the SAP flow. A suitable actuation device for cyclically raising and lowering the adjustable gate 408 preferably does not cause excessive vibrations or other movements that may cause the scales 342 to read inaccurately.

Referring now to FIG. 8, it has been found that a "combining drum"-type vacuum draw roll 800 may be advantageously used in conjunction with vibratory feeders 332, such as those described herein, or, alternatively, with other SAP feed devices and methods, such as those that are known in the art. The combining drum 800 is characterized in that several or all of the parts that eventually form the absorbent core 6 of the garment 10 are assembled in a continuous motion around all or part of the combining drum's circumference. In a preferred embodiment, the combining drum 800 combines the first casing sheet supply 316, opened tow 312, SAP 326 and second casing sheet supply 318 (i.e., various constituent parts of the core composite 348, which may, of course, include other parts) in a substantially continuous operation as they are conveyed by the combining drum 800. Each of the parts may be conveyed to the combining drum 800 separately and then joined together into an integrated structure, or alternatively, some of the parts may be joined to one another prior to contact with the combining drum 800. For example, an additional layer 20 may be affixed to either side of one or both of the first and second casing sheet supplies 316, 318 before the supply is provided to the combining drum 800.

As noted before, a preferred combining process has been generally described elsewhere herein with reference to Locations A, B, C and D of FIG. 3. The operation of the combining drum 800 described herein is relatively simple compared to many known core-forming apparatus, and may be adapted to operate at high line speeds. For example, it is anticipated that the combining drum 800 may be adapted to operate with an assembly line producing in excess of 600 diapers per minute.

In a preferred embodiment the combining drum 800 has a generally cylindrical surface 802 with a vacuum surface 804 forming a circumferential belt on the cylindrical surface 802. The vacuum surface 804 comprises one or more holes 806 through which a vacuum is applied to the various parts of the core composite 348. The holes 806 in the vacuum surface 804 may be formed by any means known in the art, such as drilling, machining, casting and so on. In a preferred embodiment, the holes 806 have a diameter of about 0.0625 inches to about 0.75 inches, and more preferably of about 0.125 inches to about 0.625 inches, and most preferably of about 0.25 inches to about 0.50 inches. Also in a preferred embodiment, the holes may be spaced from one another by a center-to-center distance of about 0.10 inches to about 1.00 inch. The holes may be spaced in a rectilinear array, as staggered rows, or in any other pattern that conveys the desired amount of vacuum. The vacuum surface 804 also may comprise any other relatively rigid foraminous structure, such as one or more mesh screens or removable perforated plates that are affixed to openings in the cylindrical surface 802. In a preferred embodiment, the combining drum 800 may also comprise landing areas 808 on either side of the vacuum surface 804 which may be treated to enhance their ability to grip the first and second casing layer supplies 316, 318. A vacuum is applied to the combining drum 800 through a vacuum port 810.

Figure 9:
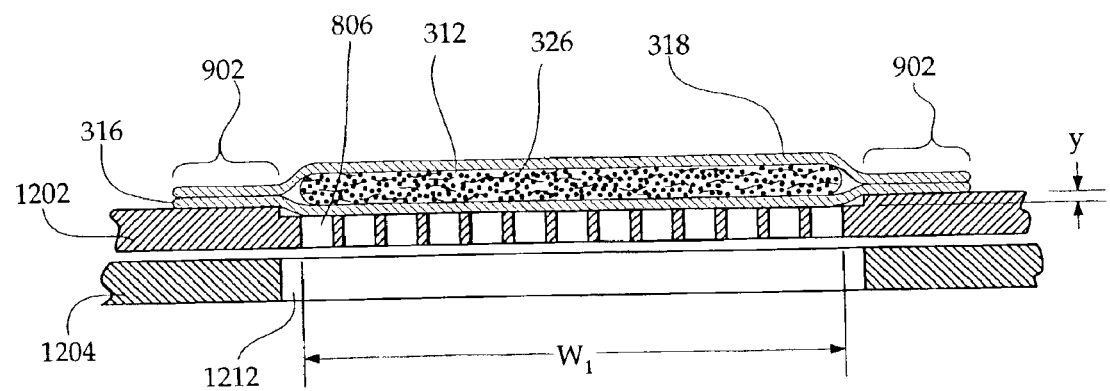
FIG. 9 is a sectional view of the vacuum surface of a combining drum according to a preferred embodiment of the present invention, shown operating with the core composite adjacent the vacuum surface.

Referring now to FIG. 9, there is shown a sectional view of the vacuum surface 804 region of a combining drum 800 as is appears just after combining the first casing sheet supply 316, opened tow 312, SAP 326 and second casing sheet supply 318 into an integrated core composite 348. The width $W_1$ of the vacuum surface 804 (as measured in a direction parallel to the rotational axis of the combining drum 800) preferably corresponds approximately to the width of the opened tow 312 and to the width of the portion of the feed tray 334 from which SAP 326 is provided. The first and second casing sheet supplies 316, 318 are preferably wider than the opened tow 312, and their excess width is located in side areas 902 that overlie the landing areas 808. The first and second casing sheet supplies 316, 318 preferably are joined to one another in their side areas 902 by adhesive bonding, other methods described elsewhere herein or by other methods known in the art. As noted elsewhere, a lay on roll 330 may be used to help join the first and second casing sheet supplies 316, 318 by use of pressure, crimping nodules, and the like.

In a preferred embodiment, the vacuum surface 804 is recessed in the cylindrical surface by a depth y of less than about 0.50 inches, and more preferably by less than about 0.10 inches, and most preferably by about 0.030 inches. It has been found that having a slight increase in the diameter of the combining drum 800 on either side of the vacuum surface 804 (i.e., a recessed vacuum surface 804) helps keep the first casing sheet supply 316 stretched across the combining drum 800 during operation.

The vacuum surface width $W_1$ may be selected to provide certain benefits to the garment into which the core composite 348 is being integrated. In one embodiment, the core composite may be integrated into the garment in a flat state, in which case it may be desirable to make the vacuum surface width $W_1$ and the width of the opened tow 312 equal to the desired width of the garment's absorbent core 6. However, the core composite 348 may be stretched, folded, or otherwise resized during manufacture, in which case the vacuum surface width $W_1$ should be correspondingly adjusted. In a preferred embodiment, the core composite 348 is folded at least once before being integrated into the garment. Folded absorbent cores have been discussed in more detail elsewhere herein. In a preferred embodiment, the vacuum surface width $W_1$ is about 1.75 inches to about 12 inches, and more preferably about 2.75 inches to about 10 inches, and most preferably about 3.75 inches. In order to reduce SAP loss during core formation, the vacuum surface width is preferably slightly narrower (about 0.10 inches on either side) than the width of the supply of opened tow 312 to promote a slight inward migration of SAP away from the side areas 902.

As noted before, it has been a continuing challenge to provide the desired distribution of SAP within the absorbent cores 6 of absorbent garments 10. It has been found that a combining drum 800 as described herein may be beneficially used to help provide such desired SAP distributions. Cellulose acetate opened tow 312 and other types of low density fibrous opened tow structures allow a relatively large amount of air to pass through them compared to conventional fluff pulp materials, and the location of the SAP 326 may be effectively controlled by modulating the amount and position of the vacuum applied to the SAP/opened tow mixture. It has been found that the distribution of the SAP can be more easily controlled with tow/SAP cores than with fluff/SAP cores. As air passes through the opened tow 312 into the vacuum it conveys the SAP 326 through the fibrous structure, and the SAP particles 326 generally tend to concentrate more densely at areas having a high vacuum. Also, as the vacuum is increased, the SAP particles 326 generally move closer to the surface of the opened tow 312 that is adjacent the combining drum 800. The degree to which the SAP migrates towards the high vacuum areas may also be affected by the duration of time that the vacuum is applied to the SAP 326. The vacuum also helps prevent SAP 326 from escaping out of the opened tow 312 during manufacturing. It has been found that a desirable mixture of SAP 326 within the opened tow 312 and reduced SAP loss may be produced using a vacuum of about 2.50 inches of water to about 20 inches of water, and more preferably of about 3.75 inches of water to about 12.5 inches of water, and most preferably of about 5.0 inches of water. The vacuum may be pre-set or may be manually or actively controlled by a control system 320 using an open-or closed-loop feedback system.

In addition to being useful for providing a homogeneous dispersion of SAP 326 in the opened tow 312, a combing drum 800 as described herein may also be used to accomplish various other desirable SAP distribution patterns. In one embodiment, the vacuum level may be modulated to provide a desirable depth of SAP penetration throughout the opened tow 312 or only in discrete areas of the opened tow 312. In other embodiments, the combining drum 800 may be adapted to provide machine direction (MD) and cross-machine direction (CD) zoning of the SAP particles 326 that provide the garment 10 with zoned absorbency. The machine direction is the direction in which a part or assembly moves during processing, and the cross-machine direction is perpendicular to the MD. The machine direction generally corresponds to the longitudinal dimension 100 of the fully-assembled garment 10 (see FIG. 1), and the cross machine direction corresponds to the lateral dimension 102 of the garment, however other relationships may also be used and are within the scope of the present invention.

Figure 10:
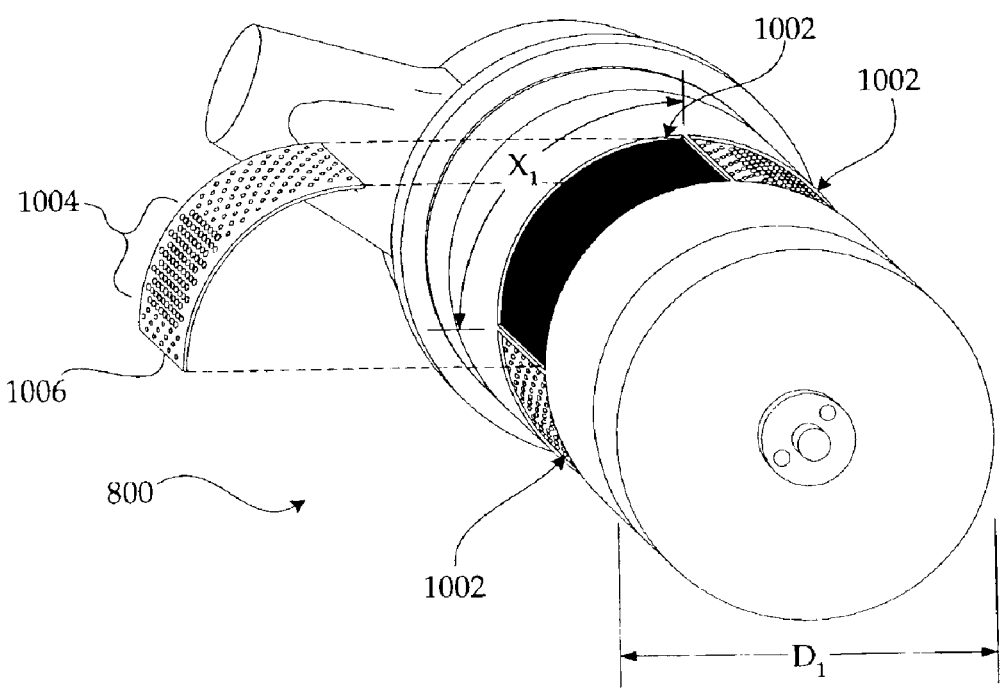
FIG. 10 is a partially exploded isometric view of another combining drum according to a preferred embodiment of the present invention.

Referring now to FIG. 10, regions of high SAP concentration, and thus greater absorbency, may be provided in the MD and CD by making the vacuum surface 804 with particularly designed target regions 1002 that convey a greater amount of vacuum to portions of the opened tow 312. Such target regions 1002 may have larger holes and/or a greater concentration of holes in those areas where a greater concentration of SAP 326 is desired. The larger amount of open space provided in such regions will allow a greater amount of airflow into the vacuum, and thus cause a greater amount of SAP to migrate to those areas. For example, in the embodiment of FIG. 10, the region 1004 has a greater concentration of larger holes, which should provide a SAP concentration in the portion of the core composite 384 adjacent region 1004. The particular pattern of SAP concentration may be adjusted by making each of the target regions 1002 from a removable plate 1006 having the desired hole pattern. Substitute plates 1006 may be easily machined to provide different hole patterns and zoned absorbency patterns.

Figure 11:
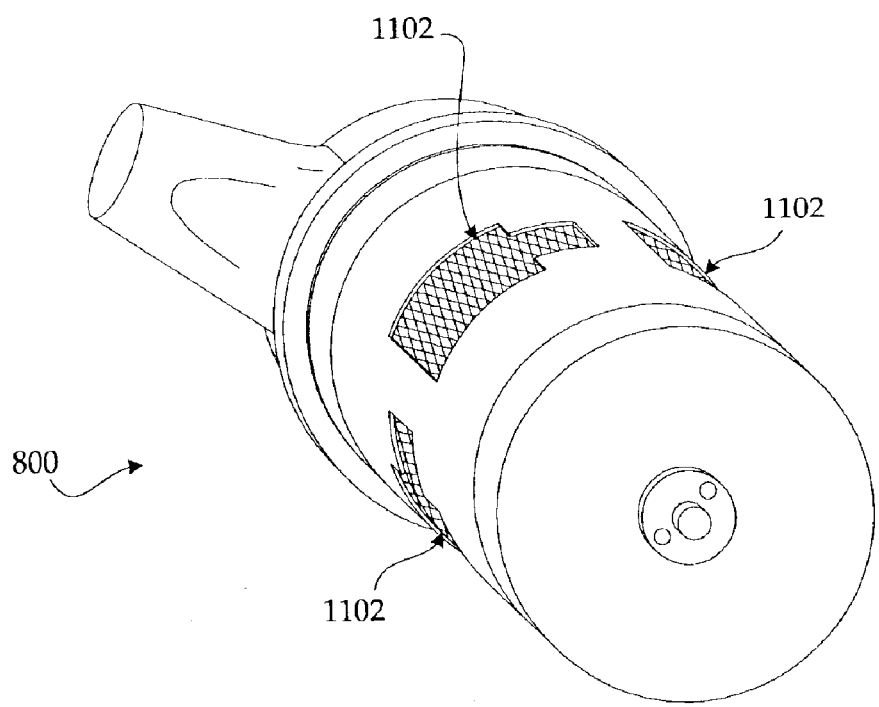
FIG. 11 is an isometric view of yet another combining drum according to a preferred embodiment of the present invention.

In another embodiment, shown in FIG. 11, the vacuum surface 804 may be separated into discrete target regions 1102, which may have varying widths, to provide zones of high and low MD and CD SAP concentrations.

In an embodiment in which the combining drum 800 has target regions 1002, 1102 for providing zoned absorbency, the combining drum diameter $D_1$ should be selected so that the corresponding parts of each target regions 1002, 1102 are spaced from one another around the circumference of the combining drum 800 by a distance corresponding to the absorbent core length $X_1$. By using such a spacing, each target region 1002, 1102 will create a targeted zone of SAP that will be properly located in each absorbent core 6 that is cut from the core composite 348.

It should be understood that by providing a distance between corresponding parts of each target region 1002, 1102 that is approximately equal to a core length $X_1$, the circumference of the combining drum 800 will be sized to equal a whole number multiple of the core length $X_1$. At a minimum, the circumference can equal one core length $X_1$, but in such an embodiment, the various parts of the core composite 348 will be in contact with the vacuum for relatively little time, which may lead to inadequate SAP distribution or other forming problems. Smaller diameter drums may also be subject to greater vibration. These problems may become exacerbated when the vacuum drum 800 is used with higher speed assembly lines. Problems may also be exist with larger drum diameters. For example, the manufacturing tolerances for a larger diameter drum may be less precise. In addition, as the size of the drum increases the amount of startup waste may increase, particularly if a greater amount of vacuum is required for the larger drum, leading to longer vacuum stabilization times. Larger drums that require greater amounts of vacuum also may require more power to produce the necessary vacuum. It will be understood that these considerations also apply to embodiments of the invention in which the combining drum 800 does not have target regions 1002, 1102, such as in the embodiment depicted in FIG. 8.

It is preferred, therefore, that the drum diameter $D_1$ be selected so that the drum's circumference is large enough that the parts of the core composite 348 are in contact with the vacuum long enough to properly distribute the SAP without excessive vibrations, but small enough to provide the required precision and a minimal amount of startup waste. It has been found that in a preferred embodiment, the diameter $D_1$ is selected so that the circumference is equal to between three and seven core lengths $X_1$. In a preferred embodiment, the combining drum 800 (whether it has target regions 1002, 1102 or not) has a diameter $D_1$ of about 6 inches to about 28 inches, and more preferably of about 9 inches to about 20 inches, and most preferably of about 12 inches. In this embodiment, the number of wasted cores caused by vacuum hysteresis or other startup-related issues has been found to be about 5 products per startup, as compared to up to about 50 products per startup with conventional core forming processes. It has also been found that providing the necessary vacuum to such a combining drum 800 requires about 10 horsepower to 20 horsepower, whereas conventional core forming systems require up to about 400 horsepower, and so a significant power savings is provided.

Figure 12:
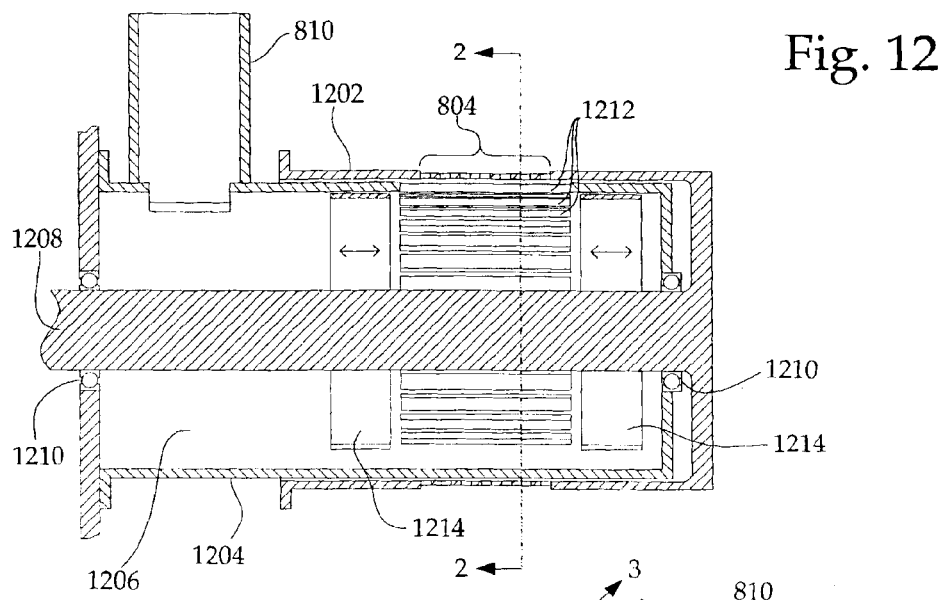
FIG. 12 is a cross sectional view of a combining drum assembly according to a preferred embodiment of the present invention as viewed from a direction orthogonal to the rotating axis of the combining drum, and as seen from reference line 3—3 of FIG. 13.
Figure 13:
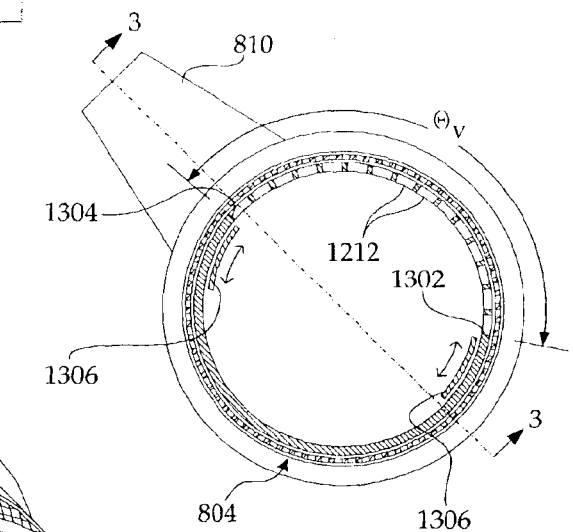
FIG. 13 is a cross sectional view of the combining drum assembly of FIG. 12, as seen from reference line 2—2.
Figure 14:
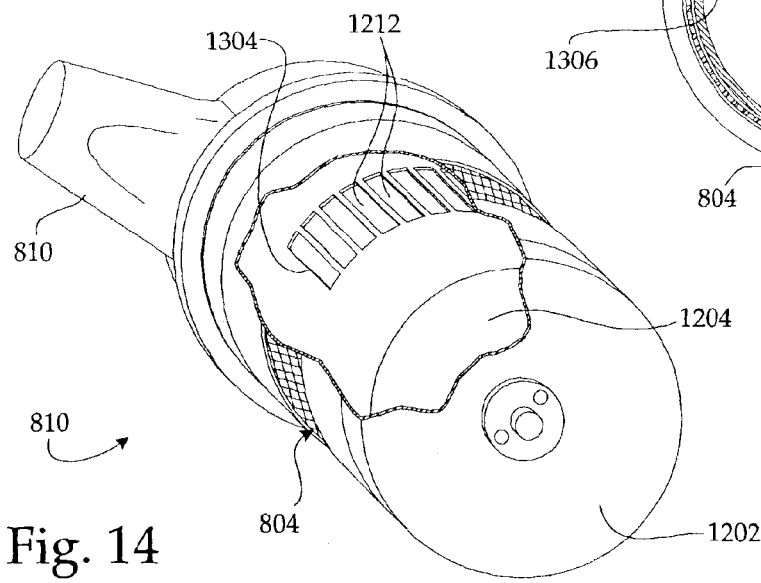
FIG. 14 is a partially cut away view of the combining drum assembly of FIG. 12, shown with the outer drum partially removed.

Referring now to FIGS. 12 through 14, a preferred embodiment of the combining drum is shown in which the combining drum 800 may be configured to apply a vacuum to the parts of the core composite 348 only through a portion of the drum's rotation. The combining drum 800 of a preferred embodiment comprises an outer drum 1202 that is positioned to rotate about a fixed inner drum 1204 by, for example, being affixed to an axle 1208 that passes through rotary bearings 1210 in the inner drum 1204. Such bearings 1210 may be equipped to reduce or prevent the leakage of the vacuum through them. A vacuum is applied to the space 1206 inside the inner drum by a vacuum port 810. The vacuum is conveyed to the outer drum's vacuum surface 804 by way of one or more passages 1212 through the inner drum 1204 that are preferably located subadjacent the path of the vacuum surface 804 of the outer drum 1202 to maximize the strength of the vacuum applied through the vacuum surface 804. It will be understood by those skilled in the art that the inner drum 1204 may be replaced by any vacuum chamber having one or more passages 1212 that convey a vacuum to a location subadjacent all or part of the vacuum surface 804.

Only those portions of the vacuum surface 804 that are immediately adjacent the passages 1212 receive a vacuum, so the duration and location of the vacuum's application may be modified by changing the size, number, or location of the passages 1212. Referring specifically to FIG. 13, the passages 1212 may be positioned through an arc of the inner drum 1204 that defines a vacuum zone $\Theta_v$. The leading edge of the vacuum zone 1302 is preferably located proximal to the point at which the first casing sheet supply 316 contacts the combining drum, which is designated as Location A in FIG. 3. The trailing edge of the vacuum zone 1304 is preferably located beyond (as the drum rotates) the point at which the second casing sheet supply 318 contacts the combining drum 800, which is designated as Location D in FIG. 3. Referring now to FIG. 14, it can be seen that those portions of the vacuum surface 804 that are not adjacent the passages 1212 are effectively cut off from the pull of the vacuum. After the core composite 348 passes the trailing edge of the vacuum zone 1304 and reaches this blocked-off area it is released from the vacuum's hold and conveyed to other parts of the assembly line.

The size of the vacuum zone $\Theta_v$ may vary depending on where the various parts are desired to be assembled to form the core composite 348. In a preferred embodiment, the vacuum zone $\Theta_v$ is about 45 degrees to about 180 degrees, and more preferably is about 90 degrees to about 160 degrees, and most preferably is about 140 degrees.

Various devices may be employed with the combining drum 800 to modulate the location and amount of vacuum applied to the core composite 348. In one embodiment, shown in FIG. 13, internal sleeves 1306 or other valving mechanisms may be used to adjust the points at which the vacuum zone $\Theta_v$ begins and ends. In another embodiment, shown in FIG. 12, other internal sleeves 1214 or other valving mechanisms may be used to narrow or widen the width of the vacuum zone $\Theta_v$, thereby effectively narrowing and widening the width $W_1$ of the vacuum surface 804. In still another embodiment, an internal sleeve or other valving mechanism may be used to reduce the vacuum level within all or part of the inner drum 1204. Any of such sleeves and valving mechanisms may be actuated by a control system 320 under the guidance of an open- or closed-loop feedback system. Greater or lesser amounts of vacuum may also be applied in discrete portions of the vacuum zone $\Theta_v$. Other designs will be obvious to one skilled in the art based on the teachings provided herein.

A combining drum 800, as described herein, may be used with any SAP feeding device that deposits SAP onto opened tow or other fibrous materials. The embodiments of the combining drum 800 described herein have been found to be particularly useful when used in conjunction with the vibratory feeder 332 as described herein.

The present invention offers several advantages over previous SAP depositing systems. In particular, the vibratory feeder 332 provides improved control over the volume and placement of the SAP 326 in the fiber, preferably the opened tow 312, allowing greater control over the SAP distribution (and zoned absorbency) during transitional phases, such as during machine startup, stopping and other speed changes, leading to fewer rejected products during such times. In addition, the vibratory feeder 332 and combining drum 800 provide improved SAP penetration into the fiber, preferably the opened tow 312 or other core material, and an improved ability to selectively position the SAP to provide desirable zoned absorbency. The vibrator feeder 332 and combining drum 800 also provide easier operation, as the various features of each device may be integrated into a control system 320. Still further, the vibratory feeder 332 and combining drum 800 are relatively simple and reliable devices that require little maintenance or cleaning, thereby reducing the operating cost of the machine. Another advantage of the vibratory feeder 332 and combining drum 800 is that they may be operated at high line speeds without detriment to the product quality. Other benefits will be apparent to those skilled in the art based on the teachings provided herein.

In another embodiment, the present invention provides an apparatus and method for forming absorbent structures that have a single casing sheet. Single-sheet absorbent cores are manufactured with a single casing sheet (rather than multiple casing sheets, as described previously herein) that is wrapped around all or part of the absorbent core material. The use of a single casing sheet has been found to provide manufacturing and economic advantages over using multiple casing sheets because the single sheet does not require slitting and rerouting, and can be bonded to itself at a single seam, rather than multiple seams as in the case of multiple casing sheets. As with multiple sheet cores, such single-sheet absorbent structures may be used in any absorbent product, including garments, such as diapers and pull-on pants, catamenial devices, absorbent wipes or sheets, and so on. Although it is known to manufacture conventional fluff pulp/SAP absorbent cores having a single casing sheet, it has been found that known methods and apparatuses for forming single-sheet core structures are not particularly useful for forming single-sheet core structures made using tow-based absorbent cores.

Figure 16A:
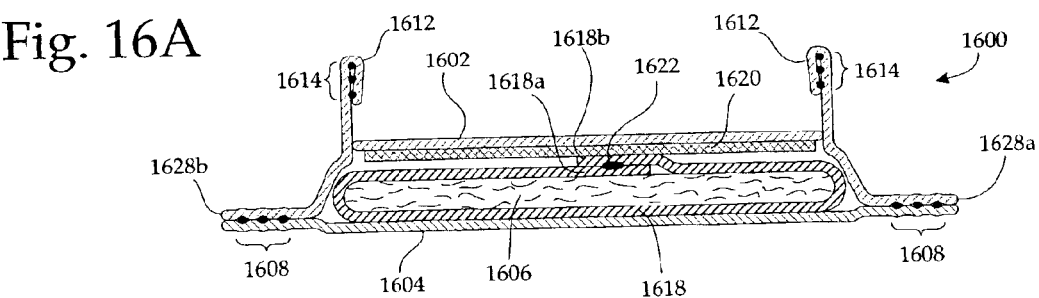
FIG. 16A is a cross-sectional view of an embodiment of an absorbent garment having a single casing sheet.
Figure 16B:
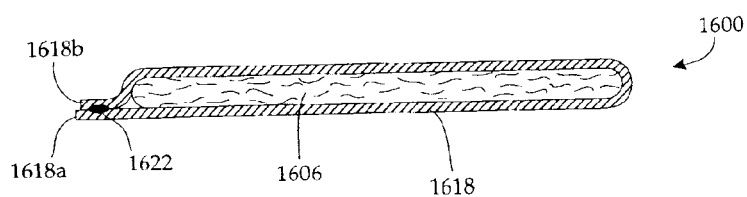
FIG. 16B is a cross-sectional view of another embodiment of an absorbent garment having a single casing sheet.

Referring now to FIGS. 16A and 16B, embodiments of single-sheet absorbent structures that may be manufactured using the present invention are shown in cross-section. In FIG. 16A, the absorbent structure is shown as it might appear when installed in an exemplary absorbent product, in FIG. 16B the structure is shown with the rest of the absorbent product omitted for clarity. The single-sheet absorbent structure comprises a tow-based absorbent core 1606 wrapped in a single casing sheet 1618. As can be seen in FIGS. 16A and 16B, the casing sheet 1618 initially may be wider than the absorbent core 1606, and then folded over the core 1606 to fully encase it. The embodiment of FIG. 16A demonstrates a tri-fold design, in which the casing sheet 1618 is folded at two locations to form three sheet portions. FIG. 16B demonstrates a bi-fold design, in which the casing sheet 1618 is folded at one location to form two sheet portions. The two ends 1618a, 1618b of the casing sheet 1618 may overlap one another so that the inside of one end 1618b abuts the outside of the other end 1618a, as shown in FIG. 16A, or may be pinch-seamed so that the two ends 1618a, 1618b abut one another on their interior sides, as shown in FIG. 16B. The ends 1618a, 1618b of the casing sheet 1618 also may abut one another without any substantial overlap, or may be attached and some or all of the overlapping portions removed before final assembly into a product. Also, in any case, the seam may be located on the top, bottom or sides of the absorbent core 1606, and may be unbonded or bonded (such as shown by bond 1622) using any known or later-developed bonding technique. Various useful compositions of the tow-based absorbent core 1606 and casing sheet 1618 have been described in more detail previously herein. In a preferred embodiment, the casing sheet 1618 comprises a sheet of tissue.

Other features of the exemplary garment 1600 of FIG. 16A include a fluid pervious topsheet 1602 and fluid impervious backsheet 1604. Garment 1600 may also have fluid pervious or impervious waste containment flaps 1612, which may contain elastic members 1614, and leg elastics 1608 adjacent the leg openings 1628a, 1628b to help control leakage. An additional layer 1620, comprising a wicking layer or the like, may also be provided in the garment 1600, and may be located inside the casing sheet 1618, outside the casing sheet 1618, or between the overlapped ends 1618*a*, 1618*b* of the casing sheet 1618. Useful materials and constructions for these and other components of exemplary garment 1600 have been described in more detail elsewhere herein.

It has been found that the present invention can be adapted to provide a continuous supply of single-sheet, tow-based absorbent core structures in an economical and effective manner. In the present invention, a vacuum draw roll, such as those described elsewhere herein, is used in conjunction with angled surfaces and other folding devices to combine the tow, SAP and casing sheet into a fully folded continuous supply of absorbent core composite material. From this continuous supply, a series of single-sheet absorbent structures may be cut to form individual absorbent cores, which may be integrated into any type of absorbent article or device or used on their own. Various embodiments of the present invention are now described with reference to FIGS. 17–29.

Figure 17:
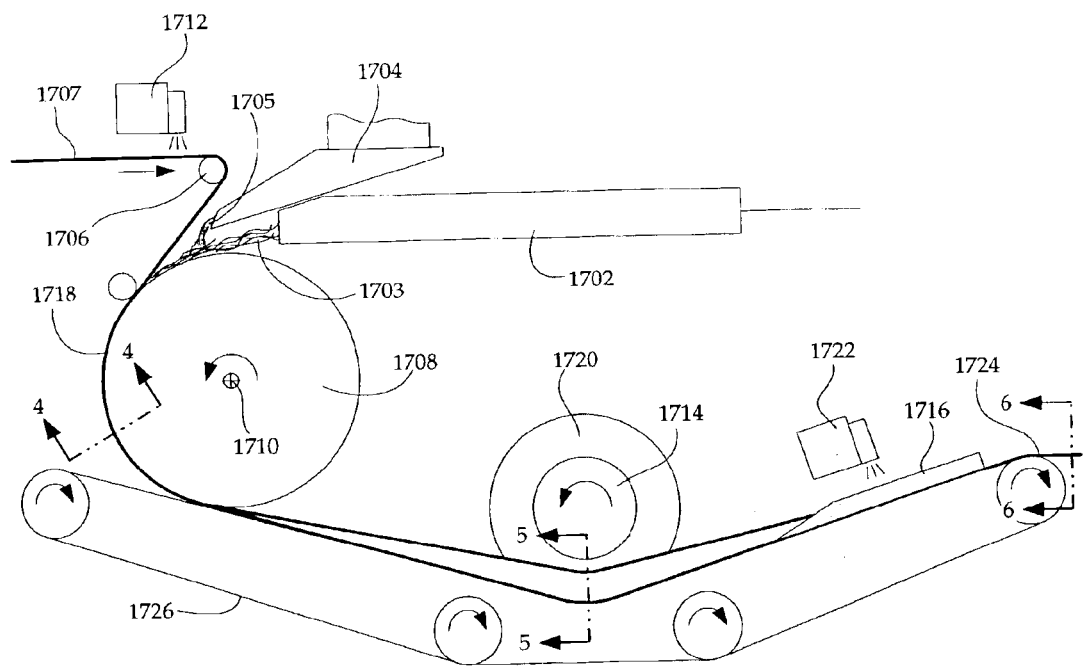
FIG. 17 is a side view of an embodiment of a system for forming tow-based absorbent structures with a single casing sheet.

In one embodiment of the present invention, shown in FIG. 17, a vacuum draw roll 1708, is operated in conjunction with a tapered break drum 1714 and folders 1716 to form and fold a single-sheet core composite supply. In this embodiment, the materials required to form the absorbent structure are provided to the apparatus by a tow supply mechanism 1702, a particulate matter supply mechanism 1704, and a casing sheet supply mechanism 1706. The tow supply mechanism 1702 may comprise any tow conveying device that provides a supply of tow, such has rollers or the like, and preferably comprises a tow forming jet, as described previously herein. The tow 1703 may be any suitable tow, as described above, for forming an absorbent structure, and preferably is a cellulose acetate tow that is opened prior to or while being supplied to the apparatus of the present invention. The particulate matter supply mechanism 1704 provides SAP and/or other additives in particulate form (which may include powders, grains, flakes, microfibers and the like) to the apparatus, and may comprise any conventional feed device, or more preferably, a vibratory feeder, such as those described herein. The casing sheet supply mechanism 1706 is shown as a single roller, but may comprise any sheet conveying device or devices, such as rollers, feed rolls, festoons, and the like, as are well known in the art, that are capable of providing a casing sheet supply 1707 (preferably a sheet of tissue) in a controlled manner to the apparatus.

With respect to the vacuum draw roll 1708, the casing sheet supply mechanism 1706, the particulate matter supply mechanism 1704 and the tow supply mechanism 1702, the embodiment of FIG. 17 may operate in much the same manner as the embodiments of these components described elsewhere herein, such as with reference to FIG. 3. More specifically, the vacuum draw roll 1708 rotates about a first axis 1710 and pulls the opened tow 1703 out of the tow supply mechanism 1702 and joins it with the casing sheet supply 1707. The particulate matter supply mechanism 1704 is positioned to deposit SAP 1705 or other particulate additives to the opened tow before it is combined with the casing sheet supply 1707. In addition, a first adhesive applicator 1712 may be positioned to spray adhesive on the portion of the casing sheet supply 1707 that contacts the tow 1703 to provide adhesion between the tow 1703 and the casing sheet supply 1707, and to adhere the SAP 1705 in place. Of course, these various components can be repositioned in various ways, and it is anticipated; for example, that the invention may be configured such that the particulate matter supply mechanism 1704 deposits the SAP 1705 directly onto the casing sheet supply 1707 or such that the first adhesive applicator 1712 sprays adhesive directly onto the tow 1703.

Figure 27:
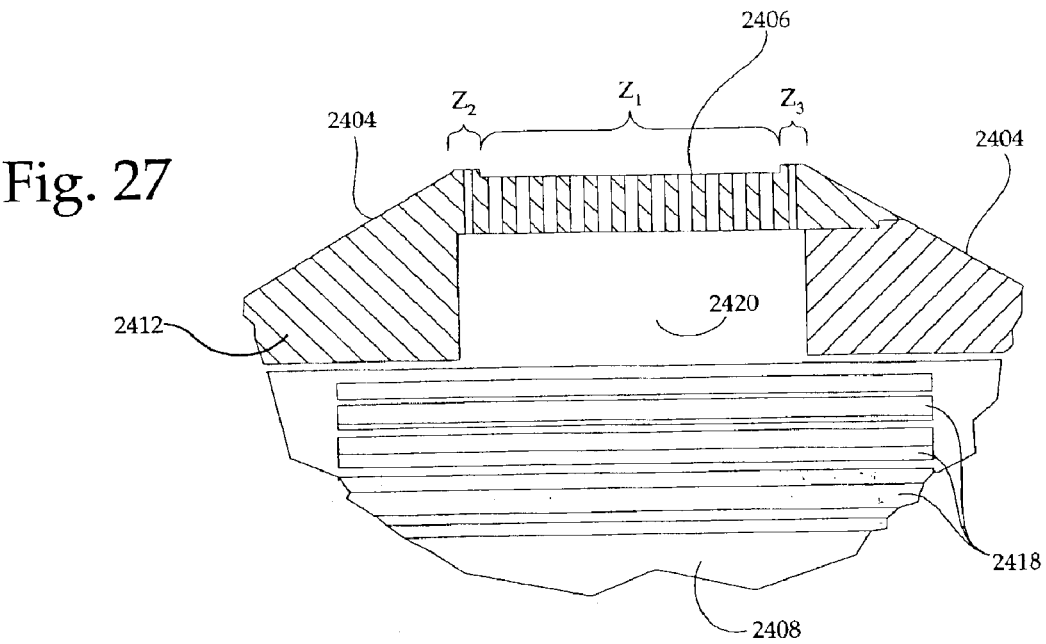
FIG. 27 is a partially cut away front view detail drawing of the embodiment of a tapered combining drum of FIG. 24.

Like the other vacuum draw rolls and combining drums described elsewhere herein, the vacuum drum has a foraminous center surface (see FIGS. 8 and 24) that applies a vacuum to the tow 1703 and casing sheet supply 1707. It has been found that relatively little vacuum is necessary, and a vacuum of about 1 to 2 inches of water, and preferably 1.5 inches of water is adequate for high speed core forming operations. The foraminous center surface may be shaped to accommodate and convey the tow 1703, and may be flat, rounded, angled, recessed and so on. In a preferred embodiment the foraminous center surface has a recessed portion, such as is shown in FIGS. 9 and 27. Other features and embodiments of the vacuum draw roll 1708 are described in more detail elsewhere herein.

In the embodiment of FIG. 17, the casing sheet supply 1707, tow 1703 and SAP 1705 (or other particulate additives) are combined on the vacuum draw roll 1708 into an unfolded open core composite supply 1718 that is open on the side that faces the vacuum draw roll 1708. For the purposes of this disclosure, the term "open core composite supply" means any composite structure having a tow material on one side and a casing sheet material on the other side, wherein the casing sheet material does not fully enclose the tow material (thus leaving the composite structure "open"). It should be noted that in this embodiment the tow 1703 is the only material between the SAP 1705 and the foraminous surface and vacuum of the vacuum draw roll 1708. It has been found that the tow 1703 has the unexpected ability to act as a filter that provides sufficient resistance to impede the flow of the SAP 1705 and prevent the loss of any substantial amount of SAP 1705 into the vacuum. After being formed, the open core composite supply 1718 preferably is transferred to a vacuum conveyor 1726 for further processing.

It has been found that a significant amount of static electricity can accumulate on the tow 1703 during the opening process when a tow forming jet is used. This static electricity can generate enough attraction between the vacuum draw roll 1714 and the open core composite supply 1718 to cause undesirable clinging that can create irregularities in the operating path of the open core composite supply 1718 and inhibit the speed at which the apparatus can operate. In order to reduce or eliminate this static charge accumulation, water may be introduced in the tow forming jet and/or on the vacuum draw roll 1714 to help reduce static accumulation and facilitate the release of the open core composite supply from the vacuum draw roll 1714.

In other embodiments, an additional layer of material (not shown), such as a wicking layer or acquisition layer may be placed on the vacuum draw roll 1708 either before or after the tow 1703 and/or casing sheet supply 1717 is applied to the vacuum draw roll 1708. In these embodiments, the absorbent core composite supply may be formed with an integral layer 1620 being incorporated directly into the structure.

Figure 18A:
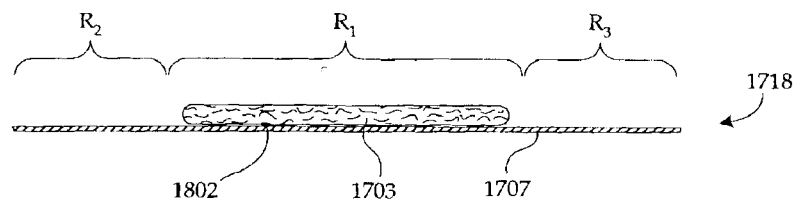
FIG. 18A is a cross-sectional view of an embodiment of an absorbent core assembly during processing in the apparatus of FIG. 17 as viewed along reference line 4—4 of FIG. 17, shown with the machinery removed for clarity.
Figure 18B:
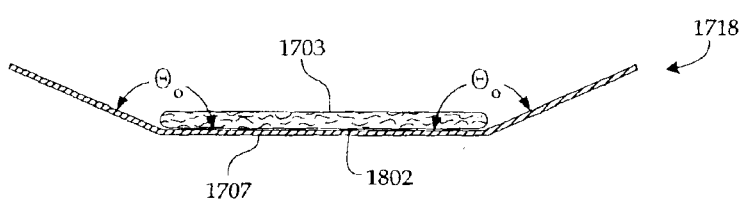
FIG. 18B is a cross-sectional view of an embodiment of an absorbent core assembly during processing in the apparatus of FIG. 17 as viewed along reference line 5—5 of FIG. 17, shown with the machinery removed for clarity.
Figure 18C:
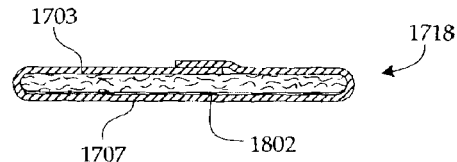
FIG. 18C is a cross-sectional view of an embodiment of an absorbent core assembly during processing in the apparatus of FIG. 17 as viewed along reference line 6—6 of FIG. 17, shown with the machinery removed for clarity.

The casing sheet supply 1707, SAP 1705 and tow 1703 are formed into a substantially flat and folded supply of core composite material in a process shown representatively by FIGS. 18A–18C. FIGS. 18A–18C are cross-sectional drawings of the core composite materials shown at reference lines 4—4, 5—5 and 6—6 in FIG. 17, respectively, with the machinery omitted for clarity. In the first step, the various materials are combined together to form an open core composite supply 1718. In the embodiment of FIG. 17, the open core composite supply 1718 is provided in a substantially flat configuration, as shown in FIG. 18A. Next, as shown in FIG. 18B, the open core composite supply 1718 is folded so that it has one or more obtuse angles $\Theta_o$ in it. Finally, the partially-folded open core composite supply 1718 is fully folded so that it is substantially flat, as shown in FIG. 18C. Although the embodiment shown in FIGS. 18A–18C depicts a tri-fold design, it will be appreciated that by using a single obtuse angle $\Theta_o$, a bi-fold design may be made. In other embodiments, such as those described subsequently herein with reference to FIGS. 21 to 27, the various steps described above, particularly the first and second steps, may be combined to improve efficiency, reduce apparatus size or obtain other benefits.

In the embodiment of FIGS. 18A–18C, The casing sheet supply 1707 preferably is wider than the tow supply 1703 so that the ends of the casing sheet supply can be folded over and joined to one another. In this embodiment, the casing sheet comprises three regions: a center region $R_1$ and first and second lateral regions $R_2$, $R_3$. The center region $R_1$ is located approximately along the centerline of the casing sheet supply 1707, while the first and second lateral regions $R_2$, $R_3$ are located on either side of the center region $R_1$. The edges of the center region $R_1$ are defined by the locations at which the obtuse angles $\Theta_o$ are made. It is also anticipated that the center region $R_1$ can be offset to one side, and one or both of the lateral regions $R_2$, $R_3$ can be folded to cover the tow to form the core composite as a bi-fold design (in which only one side region is folded) or a tri-fold design having an offset seam.

The first adhesive applicator 1712, if used, applies adhesive 1802 continuously or intermittently to the center region to adhere the tow to the casing sheet supply 1707 and hold the SAP in place. The adhesive 1802 may be applied in lines, swirls, bands or in any other useful pattern. Adhesive preferably is not applied in the lateral regions $R_2$, $R_3$ during the initial assembly stages because such adhesive might adhere to the vacuum draw roll 1708 or other machinery and interfere with manufacturing. As noted elsewhere herein, the type and amount of adhesive should be selected to minimize any detriment to the absorbing capability of the core composite, and standard construction adhesive may applied to the casing sheet supply 1707 by a standard melt blown spray adhesive applicator. The selection of adhesives, whether hydrophobic or hydrophilic, and different types of applicators will be understood by those of ordinary skill in the art. A suitable selection of adhesives and applicators will be readily apparent without undue experimentation.

In a preferred embodiment, the obtuse angles $\Theta_o$ are formed in the casing sheet supply 1707 outboard of the tow 1703, as shown in the Figures. It is also anticipated, however, that it may be useful to form the obtuse angles $\Theta_o$ at locations slightly inboard of the edges of the tow 1703 so that the tow 1703 has thicker edges. In a bi-fold design, the tow 1703 may also be folded along its centerline to form a double-thickness structure.

Figure 19:
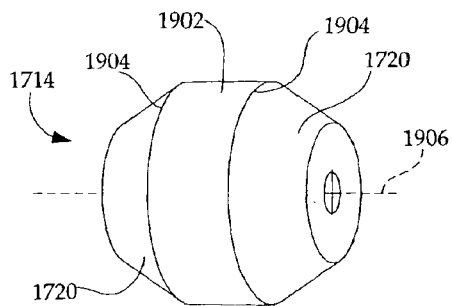
FIG. 19 is a drawing of an embodiment of a tapered break roll of the embodiment of the apparatus of FIG. 17.

The obtuse angles $\Theta_o$ may be formed in the open core composite supply 1718 by breaking the open core composite supply 1718 using one or more angled surfaces. In the embodiment of FIG. 17, the open core composite supply 1718 is conveyed over a tapered break drum 1714 having an integral pair of angled surfaces 1720. The tapered break drum is shown in more detail in FIG. 19. As shown in FIG. 19, the tapered break drum 1714 comprises a center surface 1902 (which may be cylindrical, rounded, recessed or otherwise shaped or textured) and two angled surfaces 1720. The two angled surfaces 1720 extend from a respective edge 1904 of the center surface 1902 and taper (preferably in a conical fashion) to have a smaller diameter as they proceed away from the center surface 1902. The angle of the taper, is selected to impart the desired obtuse angles $\Theta_o$ in the open core composite supply 1718. In order to minimize friction on the open core composite supply 1718, the tapered break drum 1714 preferably rotates about an axis 1906 so that the surface speed of the tapered break drum 1714 approximately matches that of the open core composite supply 1718, and is preferably designed to have a low rotational inertia to allow the drum to quickly respond to changes in operating speed. The tapered break drum 1714 is positioned in the assembly line such that it tends to create tension in the center region $R_1$ of the open core composite supply 1718, as shown, for example, in FIG. 17. When the tapered break drum 1714 is thus positioned, the side regions $R_1$, $R_2$, which are not under as much tension as the center region $R_1$, tend to follow the path of least resistance by following the contours of the angled surfaces 1720, thereby forming the obtuse angles $\Theta_o$.

Figure 20:
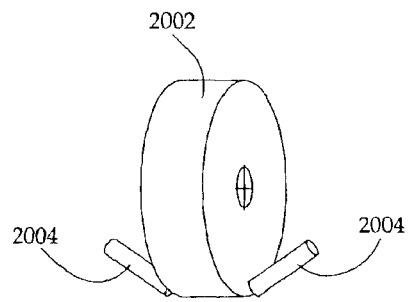
FIG. 20 is a drawing of an embodiment of angled surfaces and an untapered break drum that may be used with the embodiment of FIG. 17.

In another embodiment shown in FIG. 20, the angled surfaces may instead comprise rollers 2004 or fixed guides that are placed at angles adjacent to an untapered break drum 2002. In this embodiment, the break drum 2002 applies tension to the center region $R_1$ of the open core composite supply 1718, and the rollers 2004 impart the desired obtuse angles $\Theta_0$ in the side regions $R_1$, $R_2$ of the open core composite supply 1718.

The size of the obtuse angles $\Theta_o$ preferably are selected to increase the speed at which the open core composite supply 1718 can be folded by the folders 1716. This angle may depend on the type of folders 1716 that are employed. It is also anticipated that in a tri-fold design the obtuse angles $\Theta_o$ may be different for each side of the open core composite supply. In a preferred embodiment, the obtuse angles $\Theta_o$ are between about 130 degrees and about 175 degrees. In a more preferred embodiment, the obtuse angles $\Theta_o$ are between about 140 degrees and about 165 degrees. In an even more preferred embodiment, the obtuse angles $\Theta_o$ are about 154 degrees.

After the obtuse angle $\Theta_o$ or angles are made in the open core composite supply 1718, it is conveyed to one or more folders 1716 that fold the composite into a substantially flat folded core composite supply 1724. The folders 1716 may comprise any known folding equipment, but preferably comprise a set of folding boards that maintain substantially equal web tensions across the cross-direction of the tissue sheet (i.e., in the direction perpendicular to the machine direction. Ideally, the folding boards prevent unwanted wrinkling or buckling in the tissue sheet.

A second adhesive applicator 1722 may, in some embodiments, be provided to apply adhesive to the center or side regions $R_1$, $R_2$, $R_3$ during the folding process to hold the casing sheet supply 1707 in place once the folded core composite supply 1724 is formed. Such adhesive may be applied on either side of the casing sheet supply 1707, and may also be applied on the tow 1703. It will be appreciated that the design and location of the second adhesive applicator 1722 should be selected so that it is operatively associated with the folder 1716 such that it applies adhesive to the proper surfaces either before, during or after the folding operation performed by the folder 1716. The relative positioning of these devices, and other manners in which the second adhesive applicator 1722 may be operatively associated with the folder 1716 will be readily understood by those of ordinary in the art. In a preferred embodiment, the second adhesive applicator 1722 comprises a slot-coater that applies construction adhesive to seal the casing sheet supply 1707 after it is has been folded. The slot-coater preferably comprises a blade-like device that slips between the overlapping portions of the casing sheet supply 1707 and applies adhesive to one or both of the facing portions of the folded, but as yet unbonded, casing sheet supply 1707. Of course, the second adhesive applicator 1722 may also comprise any conventional adhesive applicator, such as a spray adhesive applicator or conventional slot adhesive applicator positioned prior to or above the folder 1716 that applies adhesive before the casing sheet supply 1707 is fully folded. After the adhesive is applied by the second adhesive applicator 1722, the folded core composite supply 1724 may be may be pressed in a pinch roller or in a debulker (not shown) to help seal the adhesive. Alternatively, or in addition to the second adhesive applicator 1722, other bonding devices or methods may be used. For example, in a bi-fold design, an edge sealer may be employed after the second adhesive applicator to attach the edges of the casing sheet supply, as shown in FIG. 16B. In still other embodiments, the casing sheet supply 1707 may not be sealed at this point, and may instead be held in its closed position by contact with other parts of a garment or other article into which the folded core composite supply 1724 is integrated.

Figure 21:
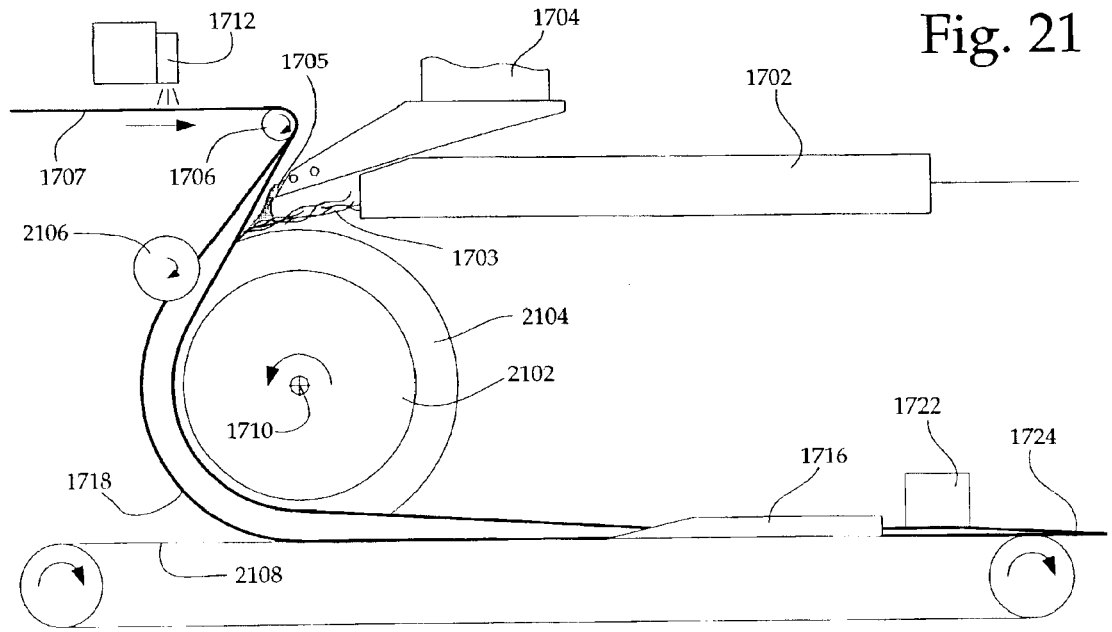
FIG. 21 is a side view of another embodiment of a system for forming tow-based absorbent structures with a single casing sheet.
Figure 22:
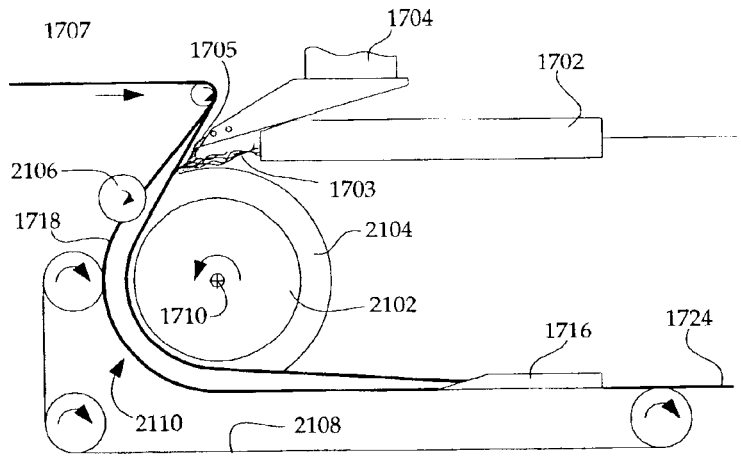
FIG. 22 is a side view of still another embodiment of a system for forming tow-based absorbent structures with a single casing sheet.

Referring now to FIG. 21, in another embodiment of the invention, the angled surfaces may be integrated into the vacuum draw roll, thereby making the apparatus more compact and removing the necessity of providing a separate break roll or other devices between the vacuum draw roll and the folders 1716. In this embodiment the vacuum draw roll is a tapered vacuum draw roll 2102 that comprises one or more angled surfaces 2104. The tapered vacuum draw roll 2102 simultaneously forms the open core composite supply 1718 and creates the obtuse angles $\Theta_o$ in the open core composite supply 1718. A vacuum conveyor 2108 then transports the open core composite supply 1718 to the one or more folding devices 1716 where it is folded into a folded core composite supply 1724. In a variation of the embodiment of FIG. 21, shown in FIG. 22, the vacuum conveyor 2108 may comprise an arcuate portion 2110 that wraps partially around the tapered vacuum draw roll 2102. It is believed that in this embodiment the presence of the arcuate portion of the conveyor may help retain the SAP 1705 or other particulate matter or additives in position during the forming operation.

Figure 23:
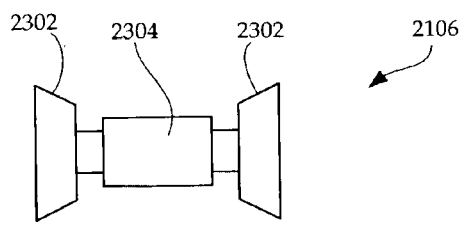
FIG. 23 is a top view of an embodiment of a stepped lay on roll that may be used with a tapered vacuum draw roll in a system for forming tow-based absorbent structures with a single casing sheet.

A tapered or stepped lay-on roll 2106 also may be used in conjunction with the embodiment of FIG. 21 to help conform the casing sheet supply 1707 to the angled surfaces 2104 of the tapered vacuum draw roll 2102. An example of a tapered lay-on roll 2106 is shown in more detail in FIG. 23. In the example of FIG. 23, the tapered lay-on roll has two tapered surfaces 2302 that abut the angled surfaces 2104 of the vacuum draw roll during use, and may optionally have a center surface 3204 having an appropriate shape (preferably cylindrical) to generally abut the center surface of the tapered vacuum draw roll 2102. In other embodiments, the tapered surfaces may be replaced by one or more cylindrical or disc-like surfaces.

Figure 24:
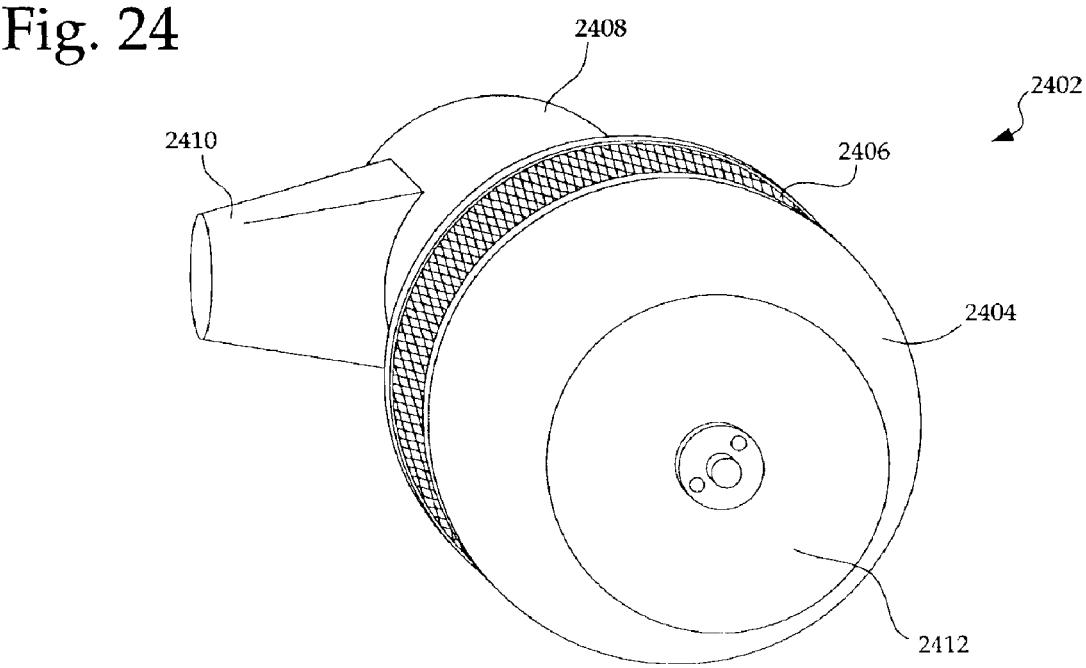
FIG. 24 is an isometric view of an embodiment of a tapered vacuum draw roll that may be used in a system for forming tow-based absorbent structures with a single casing sheet.

An embodiment of a tapered vacuum draw roll of the present invention is now described in detail with reference to FIGS. 24–27. FIG. 24 is an isometric view of a tapered vacuum draw roll 2402 showing the angled surfaces 2404 (one of which is visible) and foraminous center surface 2406. The angled surfaces 2404 and foraminous center surface 2406 are disposed on a rotatable drum 2412 that is positioned outside an inner structure 2408. The inner structure 2408 contains one or more vacuum passages to convey a vacuum to the foraminous center surface 2406. The angled surfaces 2404 preferably comprise tapered surfaces, preferably shaped as conic sections, such as those described with reference to the tapered break drum 1714 of FIGS. 17 and 19. Also shown in FIG. 24 is a vacuum port 2410 that may be connected to a vacuum source. Of course, it will be appreciated that in embodiments of the invention in which a bi-fold core design is produced, there may only be one angled surface 2404, and the foraminous center surface 2406 may not be located in the center of the rotatable drum. Also in a bi-fold design, the center surface may be peaked in the middle to break the open core composite supply 1718 along or near its centerline.

Figure 25:
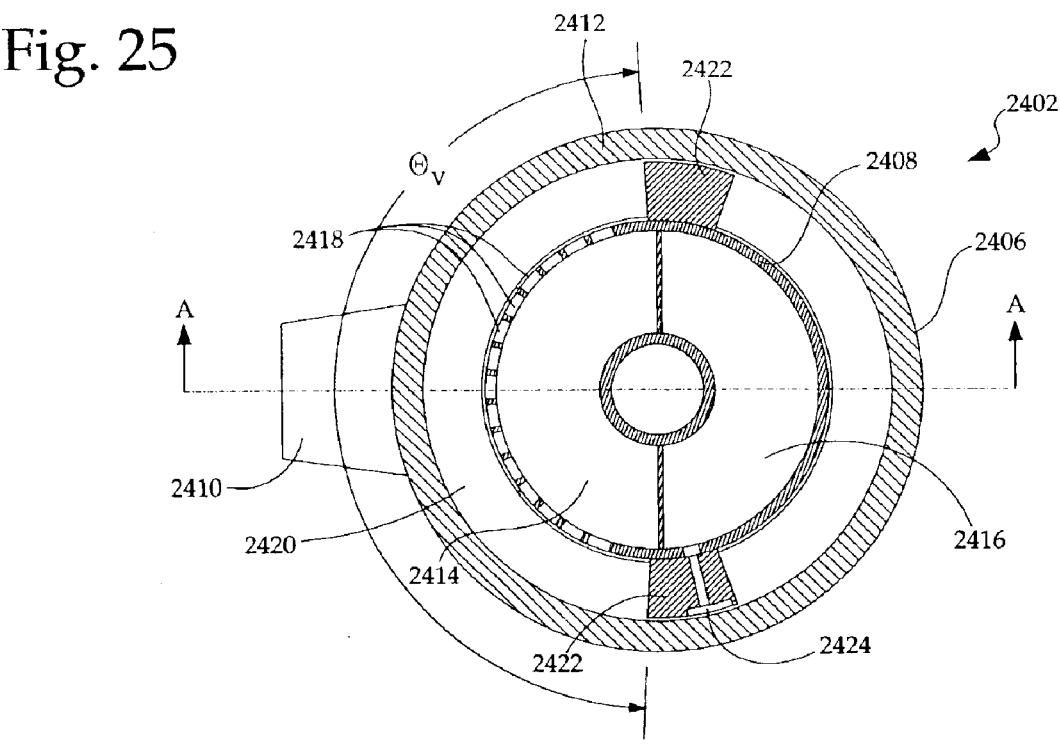
FIG. 25 is a cut away side view of the embodiment of a tapered combining drum of FIG. 24.
Figure 26:
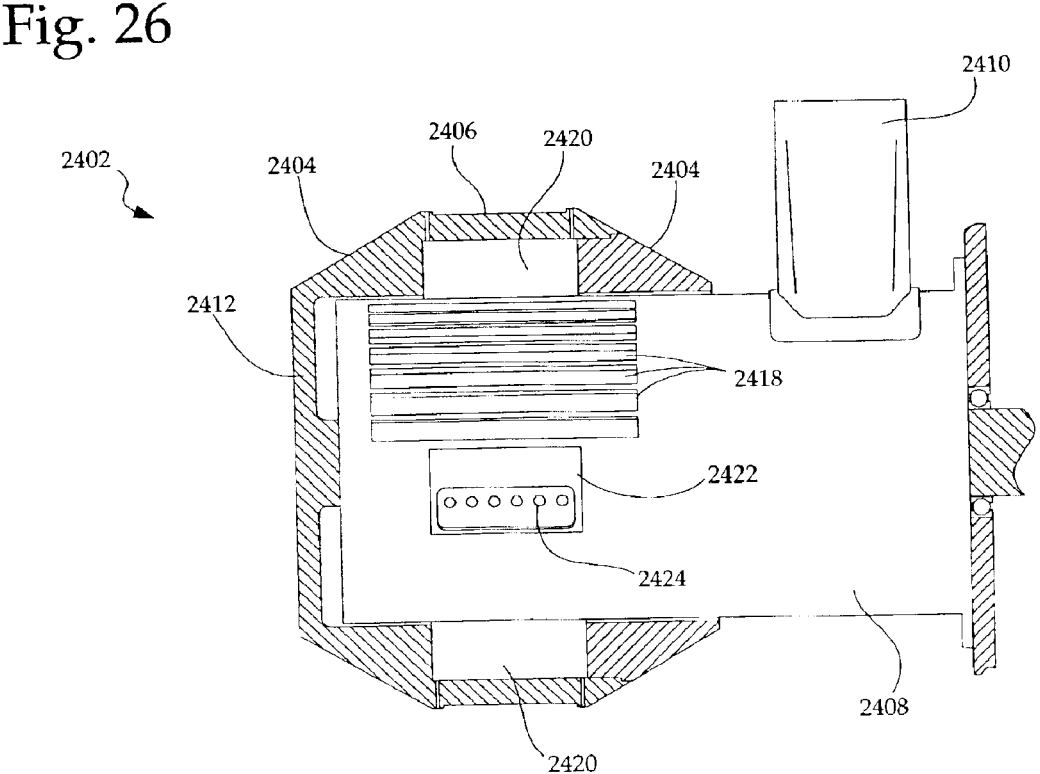
FIG. 26 is a partially cut away front view of the embodiment of a tapered combining drum of FIG. 24.

Referring now to FIGS. 25 and 26, the internal structure of tapered vacuum draw roll 2402 is described. As noted before, the tapered vacuum draw roll 2402 comprises a rotatable outer drum 2412 disposed around an inner structure 2408. For clarity, in FIG. 25 the outer drum 2412 is shown cut away at about the middle of the foraminous center surface 2406 and the passages through the foraminous center surface 2406 are omitted in both FIGS. 25 and 26. In this embodiment, the inner structure 2408 comprises a vacuum chamber 2414 to which a vacuum is provided. The inner structure 2408 also has one or more vacuum passages 2418 that place the vacuum chamber 2414 in fluid communication with the underside of the foraminous center surface. As best seen in FIG. 26, there may be a space 2420 between the foraminous center surface 2406 and the outer surface of the inner structure 2408. In order to prevent the vacuum from being applied the entire circumference of the foraminous center surface 2406, a pair of vacuum blocks 2422 are placed in the space 2420 to inhibit the fluid communication of the vacuum. As shown in FIG. 25, the placement of the vacuum blocks 2422 dictates the size of the vacuum zone $\Theta_V$ in which vacuum is applied to the foraminous center surface 2406.

In a preferred embodiment, the tapered vacuum draw roll 2402 (or any other draw roll) may be further equipped with a pressurized air blow-off port to help remove the open core composite supply 1718 for further processing. In such an embodiment, the inner structure 2408 may further comprise a pressurized chamber 2416 to which pressurized air is provided. The pressurized air in the pressurized chamber 2416 is placed in fluid communication with the foraminous center surface 2406 to expel the open core composite supply 1718 after it reaches the trailing edge of the vacuum zone $\Theta_V$. Preferably, this is accomplished by providing the vacuum block located at the trailing edge of the vacuum zone $\Theta_V$ with an air blow-off passage 2424 that is in fluid communication with the pressurized chamber 2416. As the outer drum 2412 rotates, the foraminous center surface 2406 passes over the blow-off passage 2424, and the pressurized air therein is forced out of the foraminous center surface 2406, creating a force to release the open core composite supply 1718.

The foraminous center surface 2406 may be any suitable surface having holes or slots to pass a vacuum therethrough, and preferably is similar to the vacuum surface 804 described previously herein with reference to FIG. 8. Referring now to FIG. 27, in a preferred embodiment, the foraminous center surface comprises three vacuum regions: a central vacuum region $Z_1$ and first and second lateral vacuum regions $Z_2$, $Z_3$. The central vacuum region $Z_1$ preferably is approximately the same width as the supply of tow material 1703, and is recessed to accommodate the tow 1707 to some degree as it is being conveyed. The lateral vacuum regions $Z_2$, $Z_3$, are disposed in either side of the central vacuum region $Z_1$, and contact the casing sheet supply 1707 during operation. The purpose of the lateral vacuum regions $Z_2$, $Z_3$ is to firmly hold the casing sheet supply 1707 to form a seal that inhibits the lateral escape of SAP 1705 or other additives during operation, and to improve the grip on the tow 1703 and casing sheet supply 1707 that is created in the central vacuum region $Z_1$.

In many of the embodiments described previously herein (such as the embodiments described with reference to FIGS. 17, 21 and 22), the casing sheet supply 1707 is conveyed along a portion of its path by the vacuum draw roll 1708, 2102 in such a manner that the casing sheet supply 1707 wraps around a substantial portion of the vacuum draw roll 1708, 2102. However, in other embodiments, the various devices described herein can be arranged in configurations in which a vacuum draw roll deposits tow onto a casing sheet supply that is conveyed without being wrapped around a portion of the vacuum draw roll 2808. Various embodiments having this configuration are now described with reference to FIGS. 28 and 29.

Figure 28:
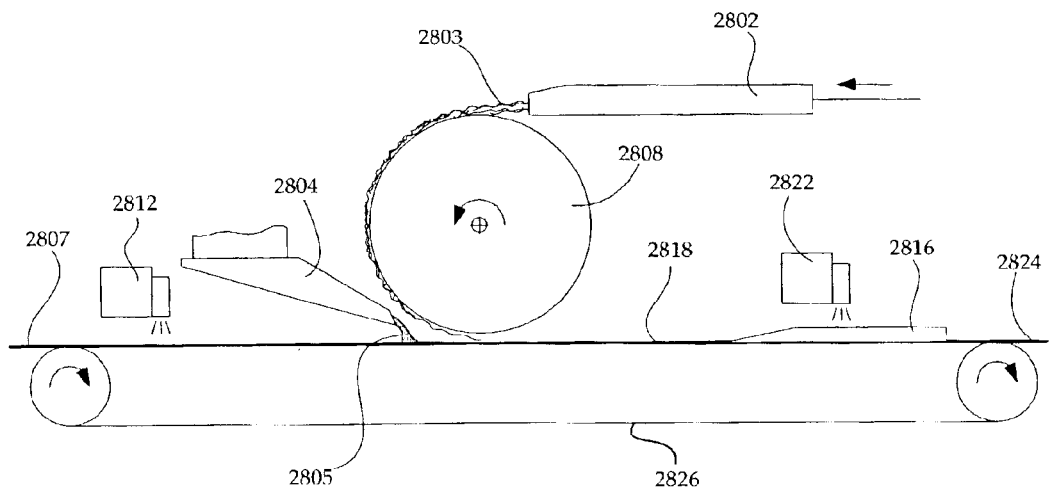
FIG. 28 is a side view of another embodiment of a system for forming tow-based absorbent structures with a single casing sheet.

Referring to FIG. 28, in one embodiment of the invention a casing sheet supply may be provided by a substantially linear conveyor 2826 (preferably a vacuum conveyor), while tow 2803 is provided by a tow supply mechanism 2802 and particulate matter such as SAP 2805 is provided by a particulate matter supply mechanism 2804. As the casing sheet supply 2807 is conveyed along the conveyor 2826, a first adhesive applicator 2812 applies adhesive to all or part of one side of the casing sheet supply 2807. Next, SAP 2805 is applied, and then the tow 2803 is deposited onto the casing sheet supply 2807 by a vacuum draw roll 2808 to form an open core composite supply 2818. The open core composite supply 2818 is then conveyed to a folder 2816 that folds it into a substantially flat, folded core composite supply 2824.

The first adhesive applicator 2812 applies adhesive to hold the SAP in place and adhere the tow 2803 to the casing sheet supply 2807. A second adhesive applicator 2822 may also be used with the embodiment of FIG. 28 to apply adhesive to either the tow 2703 or casing sheet supply 2807 to hold the folded portions of the casing sheet supply 2807 in place after it is formed into the folded core composite supply 2824. In another embodiment, the second adhesive applicator 2822 may be omitted if the first adhesive applicator 2812 is adapted to apply adhesive to the portions of the casing sheet supply 2807, such as the lateral regions $R_2$, $R_3$, that will eventually be folded over to hold the folded core composite supply 2824 together. In an embodiment in which the first adhesive applicator 2812 is used to apply adhesive to the lateral regions $R_1$, $R_2$ of the casing sheet supply, the vacuum draw roll 2808 should be positioned so that it does not contact the portions of the casing sheet supply 2807 that have adhesive applied to it in order to avoid accumulations of adhesive on the machinery. Of course other sealing devices, such as ultrasonic sealers, also may be used to form a bond to hold the folded core composite supply 2824 together.

Figure 29:
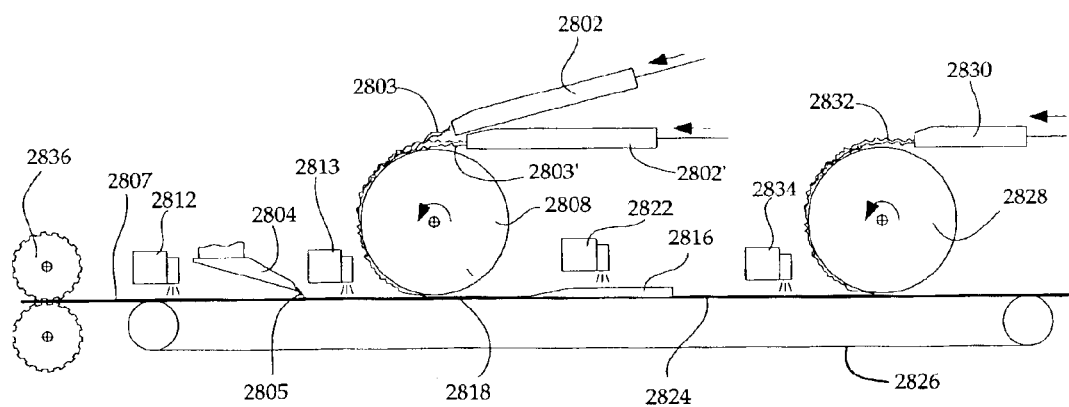
FIG. 29 is a side view of yet another embodiment of a system for forming tow-based absorbent structures with a single casing sheet; and, FIG. 30 is a side view of yet another embodiment of a system for forming tow-based absorbent structures with a single casing sheet.

Embodiments in which the casing sheet supply 2807 is not conveyed around the vacuum draw roll 2808 provide the advantage that the apparatus can be reconfigured relatively easily to modify or supplement the assembly process. For example, as shown in FIG. 29, a third adhesive applicator 2813 may be included between the particulate matter supply mechanism 2804 and the vacuum draw roll 2808 to provide another layer of adhesive to hold the SAP 2805 in place and/or to adhere the tow 2803 to the casing sheet supply 2807. In such an embodiment, the first adhesive applicator 2812 may optionally be omitted.

FIG. 29 also demonstrates other features that may be used with any embodiment of the invention. For example, a second tow supply mechanism 2802' may be used in conjunction with the original tow supply mechanism 2802 to provide a second supply of tow 2803' and thereby create a multi-component or multi-layered tow. In such an embodiment the second supply of tow 2803' may be placed under, above, or next to the original supply of tow 2803. Also shown in FIG. 29 are a second vacuum draw roll 2828 and a fourth adhesive applicator 2834 that may be used to attach an additional supply of tow 2832 to the folded core composite supply 2824. The additional supply of tow 2832 may be used, for example, as an acquisition layer or as a transfer layer, or may be infused with an additional supply of SAP (not shown) to act as an additional absorbent layer.

FIG. 29 also demonstrates an embossing roll 2836 that may be used in conjunction with the invention to emboss the casing sheet supply 2807. The pattern of the embossing roll 2836 may be selected to form wells, microwells or grooves in the surface of the casing sheet supply 2807. The SAP 2805 deposited on the casing sheet supply 2807 may concentrate in these wells or grooves, thereby creating zones of greater or lesser absorbency in the completed core composite supply 2824. These zones can subsequently be positioned into absorbent garments to provide targeted regions of high absorbency. The embossing provided by the embossing roll 2836 also may add loft or a more desirable texture to the structure of the finished absorbent garment or provide other benefits.

Although FIGS. 28 and 29 and the discussion thereof describe the casing sheet supply 2807 as being conveyed in a substantially linear fashion by conveyor 2826, it is also envisioned that conveyor 2826 may have a non-linear path, such as the conveyor 1726 in FIG. 17, with the vacuum draw roll 2808 being located at the point at which conveyor 2826 is inverted or elsewhere. All such variations are within the scope of the present invention.

Although the tow supply mechanisms described thus far (i.e., items 1702, 2802, 2802' and 2830) have generally depicted tow forming jets, it will be understood by those of ordinary skill in the art that the tow supply mechanisms may also comprise any other type of tow-forming or tow-supplying device. Indeed, there is no requirement that the tow be opened or otherwise conditioned "on the fly" during the manufacturing process. Instead, in other embodiments of the invention the tow may be substantially fully prepared in a separate manufacturing operation, and supplied to the present invention as a roll good. As used herein, "roll good" refers to any pre-made supply of material that requires little or no further substantive processing as it is supplied to the present invention. A roll good preferably is provided in roll form, but also may be provided as sheets, as a folded supply, as a continuous or discontinuous supply, or in any other suitable manner, as will be apparent to those of ordinary skill in the art.

Figure 30:
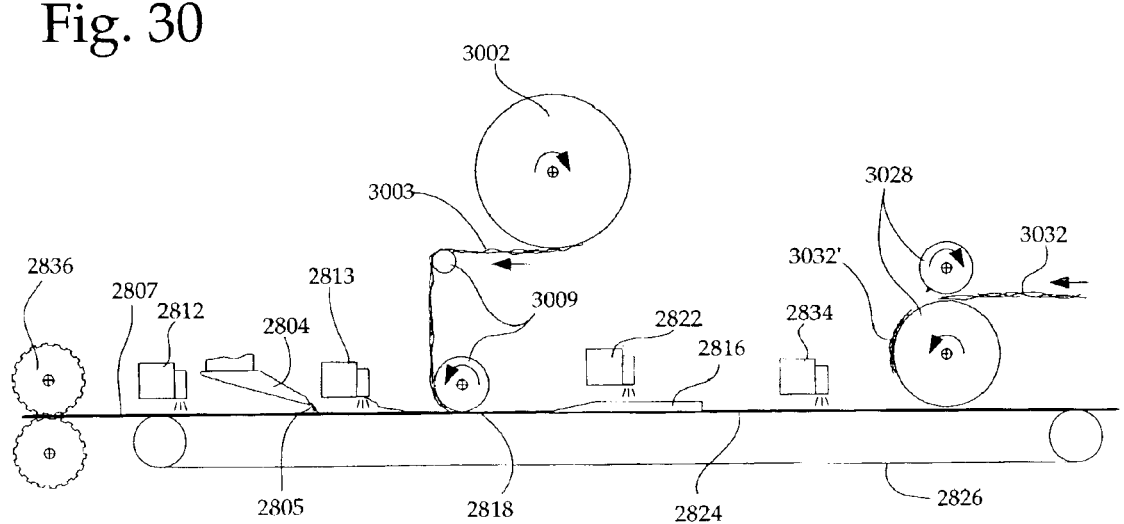

FIG. 30 depicts an apparatus similar to that of FIG. 29, except that the tow supply mechanisms comprise various types of roll good tow supply mechanisms. As shown in FIG. 30, a first roll good tow supply 3003 that forms the absorbent core 2824 may be provided as a continuous supply from a wound reel 3002 of roll good tow material. A conventional tissue unwinding mechanism or other suitable device may be used to control the feed rate of the first roll good tow supply 3003. Various rollers 3009 may be used to convey the first roll good tow supply 3003 and press it to the casing sheet supply 2807. A second roll good tow supply 3032 also may be supplied to overlie the folded core composite supply 2824 to act as an acquisition layer, transfer layer or the like. In the embodiment of FIG. 30, the second roll good tow supply 3032 is severed into discrete pieces 3032' that are spaced apart and placed onto the folded core composite supply 2824 using, for example, a conventional vacuum transfer roll and cutting knife assembly 3028. Of course, the second roll good tow supply 3032 may be provided by any other suitable device, and need not be provided as discontinuous pieces.

Other embodiments, uses, and advantages of the invention will be apparent to those skilled in the art from consideration of the specification and practice of the invention disclosed herein. Furthermore, the present invention may be used in combination with any suitable prior art apparatus or methods, and any description herein of drawbacks or limitations of the prior art are not to be understood as limiting the scope of the present invention to necessarily exclude the inclusion of such prior art apparatus or methods with the present invention. For example, it is envisioned that a second tissue layer or other casing layer may be used with the present invention to overlie the absorbent core to provide additional tensile strength or fluid handling characteristics. The specification should be considered exemplary only, and the scope of the invention is accordingly intended to be limited only by the following claims and equivalents thereof.

We claim:

1. An apparatus for forming absorbent structures having a single casing sheet, the apparatus comprising:
   a tow supply mechanism for providing tow material;
   a particulate matter supply mechanism for providing particulate matter;
   a casing sheet supply mechanism for providing casing sheet material;
   a vacuum draw roll comprising a foraminous center surface, the foraminous center surface having a width defined by a first edge and a second edge and being rotatable about a first axis, the vacuum draw roll being positioned to receive the tow material, the particulate matter and the casing sheet material to form a open core composite supply;
   one or more angled surfaces positioned to create one or more obtuse angles in the open core composite supply; and,
   one or more folders to further fold the one or more obtuse angles in the open core composite supply to form a folded core composite supply.

2. The apparatus of claim 1, wherein the tow material comprises cellulose acetate tow.

3. The apparatus of claim 1, wherein the tow material comprises a roll good.

4. The apparatus of claim 1, wherein the particulate matter comprises superabsorbent particles.

5. The apparatus of claim 1, wherein the casing sheet material comprises tissue.

6. The apparatus of claim 1, wherein the particulate matter supply mechanism is a vibratory feeder.

7. The apparatus of claim 1, where in the tow supply mechanism is a tow forming jet.

8. The apparatus of claim 1, wherein:
   the casing sheet material comprises a center region and first and second side regions located on opposite sides of the center region, the first side region extending from a first side of the center region to a first edge of the casing sheet material, and the second side region extending from a second side of the center region to a second edge of the casing sheet material;
   the casing sheet material is wider than the tow material;
   the tow material is positioned adjacent to the center region of the casing sheet material in the open core composite supply; and,
   the one or more angled surfaces are positioned to create a first obtuse angle proximal to the first side of the center region, and a second obtuse angle proximal to the second side of the center region.

9. The apparatus of claim 8, further comprising a first adhesive applicator positioned before the vacuum draw roll to apply adhesive to the center region of the casing sheet material.

10. The apparatus of claim 8, further comprising a second adhesive applicator operatively associated with the one or more folders and positioned to apply adhesive to at least one of the first and second side regions.

11. The apparatus of claim 1, wherein the one or more angled surfaces are operatively associated with the vacuum draw roll.

12. The apparatus of claim 11, wherein the one or more angled surfaces comprise first and second tapering surfaces, each of the first and second tapering surfaces extending from a respective edge of the foraminous center surface and tapering inward from the center surface towards the first axis.

13. The apparatus of claim 1, further comprising a break drum positioned between the vacuum draw roll and the one or more folders, the break drum being rotatable about a second axis and comprising a center surface, the center surface having a width defined by a third edge and a fourth edge.

14. The apparatus of claim 13, wherein the one or more angled surfaces are operatively associated with the break drum.

15. The apparatus of claim 14, wherein the one or more angled surfaces comprise first and second tapering surfaces, each of the first and second tapering surfaces extending from a respective edge of the center surface and tapering inward from the center surface towards the second axis.

16. The apparatus of claim 1, further comprising an open core composite supply conveyor, the open core composite supply conveyor being positioned to convey the open core composite supply from the vacuum draw roll to the one or more folders.

17. The apparatus of claim 16, wherein the open core composite supply conveyor comprises an arcuate region substantially adjacent to a sector of the vacuum draw roll.

18. The apparatus of claim 1, wherein the vacuum draw roll further comprises:
   a rotatable outer drum, wherein the foraminous center surface is disposed on the rotatable outer drum; and
   an inner structure disposed at least partially within the rotatable outer drum and comprising a vacuum chamber, the vacuum chamber having one or more vacuum passages forming a vacuum zone subadjacent at least a portion of the foraminous center surface.

19. The apparatus of claim 18, wherein the one or more angled surfaces comprise first and second tapering surfaces, each of the first and second tapering surfaces being disposed on the rotatable outer drum and extending from a respective edge of the foraminous center surface and tapering inward from the center surface towards the first axis.

20. The apparatus of claim 18, wherein the vacuum zone comprises a leading edge relative to a direction of rotation of the rotatable outer drum and a trailing edge relative to a direction of rotation of the rotatable outer drum, and the inner structure further comprises a positive air blow-off port located proximal to the trailing edge.

21. The apparatus of claim 18, wherein the foraminous center surface comprises a central vacuum region and first and second lateral vacuum regions, the first lateral vacuum region being located between the central vacuum region and the first edge of the foraminous center surface, and the second lateral vacuum region being located between the central vacuum region and the second edge of the foraminous center surface.

22. The apparatus of claim 21, wherein the central vacuum region is recessed.

23. The apparatus of claim 21, wherein the tow material has an average width approximately equal to or less than a width of the central vacuum region, and the central vacuum region is positioned to receive substantially the entire width of the tow material.

24. The apparatus of claim 23, wherein the first and second lateral vacuum regions are positioned to apply a vacuum to the casing sheet material.

25. A method for preparing absorbent structures having a single casing sheet, the method comprising:
   providing tow material;
   providing particulate matter;
   providing casing sheet material;
   forming an open core composite supply by combining the tow material, the particulate matter and the casing sheet material on a vacuum draw roll comprising a foraminous center surface, the foraminous center surface having a width defined by a first edge and a second edge and being rotatable about a first axis;
   creating one or more obtuse angles in the open core composite supply using one or more angled surfaces; and,
   forming a folded core composite supply by folding flat the one or more obtuse angles in the open core composite supply.

26. The method of claim 25, wherein providing tow material comprises providing cellulose acetate tow.

27. The method of claim 25, wherein providing tow material comprises providing roll good tow material.

28. The apparatus of claim 25, wherein providing particulate matter comprises providing superabsorbent particles.

29. The method of claim 25, wherein providing casing sheet material comprises providing tissue.

30. The method of claim 25, wherein:
   providing casing sheet material comprises providing casing sheet material comprising a center region and first and second side regions located on opposite sides of the center region, the first side region extending from a first side of the center region to a first edge of the casing sheet material, and the second side region extending from a second side of the center region to a second edge of the casing sheet material;
   providing tow material comprises providing tow material having a width narrower than a width of the casing sheet material;
   forming the open core composite supply further comprises positioning the tow material adjacent to the center region of the casing sheet material; and,
   creating one or more obtuse angles in the open core composite supply further comprises creating a first obtuse angles proximal to the first side of the center region, and a second obtuse angle proximal to the second side of the center region.

31. The method of claim 30, further comprising applying adhesive to the center region before forming the open core composite supply.

32. The method of claim 30, further comprising applying adhesive to at least one of the first and second side regions before forming the folded core composite supply.

33. The method of claim 25, wherein forming an open core composite supply and creating one or more obtuse angles are performed simultaneously.

* * * * *